United States Patent
Manjarrez Orduño et al.

(10) Patent No.: US 11,899,017 B2
(45) Date of Patent: Feb. 13, 2024

(54) PREDICTIVE PERIPHERAL BLOOD BIOMARKER FOR CHECKPOINT INHIBITORS

(71) Applicant: Bristol-Myers Squibb Company, Princeton, NJ (US)

(72) Inventors: Nataly Manjarrez Orduño, Princeton, NJ (US); Suzanne J. Suchard, Portland, OR (US)

(73) Assignee: Bristol-Myers Squibb Company, Princeton, NJ (US)

( * ) Notice: Subject to any disclaimer, the term of this patent is extended or adjusted under 35 U.S.C. 154(b) by 810 days.

(21) Appl. No.: 16/634,833

(22) PCT Filed: Jul. 27, 2018

(86) PCT No.: PCT/US2018/044168
§ 371 (c)(1),
(2) Date: Jan. 28, 2020

(87) PCT Pub. No.: WO2019/023624
PCT Pub. Date: Jan. 31, 2019

(65) Prior Publication Data
US 2021/0123920 A1    Apr. 29, 2021

Related U.S. Application Data

(60) Provisional application No. 62/691,556, filed on Jun. 28, 2018, provisional application No. 62/582,166, filed on Nov. 6, 2017, provisional application No. 62/538,509, filed on Jul. 28, 2017.

(51) Int. Cl.
| | |
|---|---|
| *A61K 39/395* | (2006.01) |
| *C07K 16/28* | (2006.01) |
| *A61P 35/00* | (2006.01) |
| *G01N 33/574* | (2006.01) |
| *G01N 33/569* | (2006.01) |
| *A61K 45/06* | (2006.01) |
| *A61K 39/00* | (2006.01) |

(52) U.S. Cl.
CPC ....... *G01N 33/57484* (2013.01); *A61K 45/06* (2013.01); *C07K 16/2818* (2013.01); *C07K 16/2827* (2013.01); *A61K 2039/507* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,808,710 B1 | 10/2004 | Wood et al. | |
| 7,488,802 B2 | 2/2009 | Collins et al. | |
| 7,943,743 B2 | 5/2011 | Korman et al. | |
| 8,008,449 B2 | 8/2011 | Korman et al. | |
| 8,168,757 B2 | 5/2012 | Finnefrock et al. | |
| 8,217,149 B2 | 7/2012 | Irving et al. | |
| 8,354,509 B2 | 1/2013 | Carven et al. | |
| 8,609,089 B2 | 12/2013 | Langermann et al. | |
| 8,779,105 B2 | 7/2014 | Korman et al. | |
| 8,779,108 B2 | 7/2014 | Queva et al. | |
| 8,900,587 B2 | 12/2014 | Carven et al. | |
| 2011/0081354 A1* | 4/2011 | Korman | C07K 16/2818 424/152.1 |
| 2013/0017199 A1 | 1/2013 | Langermann | |
| 2013/0173223 A1 | 7/2013 | Teller et al. | |
| 2014/0341917 A1 | 11/2014 | Nastri et al. | |
| 2014/0356353 A1 | 12/2014 | Queva et al. | |
| 2015/0079109 A1 | 3/2015 | Li et al. | |
| 2019/0292259 A1* | 9/2019 | Damotte | G01N 33/57423 |
| 2020/0182858 A1* | 6/2020 | Brennan | G01N 33/6854 |
| 2020/0291122 A1* | 9/2020 | Krishnan | C07K 16/2827 |
| 2021/0171629 A1* | 6/2021 | Klippel | G01N 33/57423 |

FOREIGN PATENT DOCUMENTS

| | | |
|---|---|---|
| CN | 105828834 A | 8/2016 |
| WO | WO-2007017915 A2 | 2/2007 |
| WO | WO-2009120341 A2 | 10/2009 |
| WO | WO-2012145493 A1 | 10/2012 |
| WO | WO-2015037000 A1 | 3/2015 |
| WO | WO-2015069770 A1 | 5/2015 |
| WO | WO-2016013873 A1 | 1/2016 |
| WO | WO-2016138182 A1 | 9/2016 |
| WO | WO-2019023624 A1 | 1/2019 |

OTHER PUBLICATIONS

Alsaab et al. (2017) Front. Pharmacol. 8: 561; 1-15.*
Archilla Ortega et al. (2022) J Exp Clin Cancer Res 41: 62; 1-24.*
Attili et al. (2017) Critical Reviews in Oncology/Hematology 119: 30-39.*
Chen et al. (2022) J Pathol Clin Res 8: 268-278.*
Dempke et al. (2017) European Journal of Cancer 74: 55-72.*
Knaus et al. (2017) Curr Drug Target; 18(3): 315-331.*
Lu t al. (2019) JAMA Oncol; 5(8): 1195-1204.*
Manzoor et al. (2017) Eur. J. Immunol. 47: 144-154.*
Mazzarella et al. (2019) European Journal of Cancer 117: 14-31.*
Morandi et al. (2022) Int. J. Mol. Sci. 23: 2925; 1-15.*
Nair et al. (2018) Immunology & Cell Biology; 96: 21-33.*
Ni et al. (2017) Immunological Reviews; 276: 52-65.*
Ren et al. (2022) J Immunol 208(10): 2425-2435.*
Ruhnau et al. (2016) Mediators of Inflammation; vol. 2016, Article ID 2974605, 9 pages.*

(Continued)

*Primary Examiner* — Ilia I Ouspenski
(74) *Attorney, Agent, or Firm* — Sterne, Kessler, Goldstein & Fox P.L.L.C.

(57) ABSTRACT

The present disclosure relates to the finding that the ratio of circulating (i.e., peripheral blood) central memory T cells to circulating effector T cells in a cancer patient can predict whether a tumor has an inflammatory milieu or not. In addition, since having an inflammatory milieu ("hot tumor") is a positive factor for responding to checkpoint inhibitors, e.g., PD-1 antagonists, this assay on peripheral blood can also be used to predict a response to a checkpoint inhibitor, e.g., an antibody or an antigen-binding portion thereof that specifically binds to a Programmed Death-1 (PD-1) receptor and inhibits PD-1 activity or an antibody or an antigen binding portion thereof that binds specifically to PD-1 ligand 1 (PD-L1) and inhibits PD-L1 activity.

6 Claims, 20 Drawing Sheets

(56) References Cited

OTHER PUBLICATIONS

Wischhusen et al. (2020) Front. Immunol. 11 :951; 1-21.*
Ximenis et al. (2016) Human Immunology 77: 20-28.*
Zhu et al. (2020) Cancer Treatment Reviews 91: 102115; 1-11.*
Ahrends, T., et al., "CD4 + T Cell Help Confers a Cytotoxic T Cell Effector Program Including Coinhibitory Receptor Downregulation and Increased Tissue Invasiveness," *Immunity* 47(5):848-861, Cell Press, United States (Nov. 2017).
Appay, V., et al., "Memory CD8+ T cells vary in differentiation phenotype in different persistent virus infections," *Nature Medicine* 8(4):379-385, Nature Publishing Group, United Kingdom (2002).
Berger, C., et al., "Adoptive transfer of effector CD8+ T cells derived from central memory cells establishes persistent T cell memory in primates," *Journal of Clinical Investigation* 118(1):294-305, American Society for Clinical Investigation, United States (2008).
Boutros, C., et al., "Safety profiles of anti-CTLA-4 and anti-PD-1 antibodies alone and in combination," *Nat Rev Clin Oncol* 13(8):473-86, Nature Publishing Group, United Kingdom (2016).
Brahmer, J.R., et al., "Phase I study of single-agent anti-programmed death-1 (MDX-1106) in refractory solid tumors: safety, clinical activity, pharmacodynamics, and immunologic correlates," *J Clin Oncol* 28(19):3167-75, American Society of Clinical Oncology, United States (2010).
Callea, M., et al., "Differential Expression of PD-L1 between Primary and Metastatic Sites in Clear-Cell Renal Cell Carcinoma," *Cancer Immunology Research* 3(10):1158-64, American Association for Cancer Research Inc., United States (2015).
Chen, D.S., et al., "Oncology Meets Immunology: The Cancer-Immunity Cycle," *Immunity* 39(1):1-10, Cell Press, United States (2013).
Creelan, B.C., "Update on Immune Checkpoint Inhibitors in Lung Cancer," *Cancer Control* 21(1):80-89, H. Lee Moffitt Cancer Center and Research Institute, United States (2014).
Dronca, R.S., et al., "T cell Bim levels reflect responses to anti-PD-1 cancer therapy," *JCI Insight* 1(6):e86014, The American Society for Clinical Investigation, United States (May 2016).
"FOUNDATIONONE: Technical Information," FoundationMedicine.com, accessed at https://assets.ctfassets.net/vhribv121mne/6YRrchSINOeSu48YwuesoY/caeec492925a7d569ce4e070866f709b/F1_-_Tech_Specs.pdf on Sep. 16, 2020.
Garcia-Diaz, A., et al., "Interferon Receptor Signaling Pathways Regulating PD-L1 and Pd-L2 Expression," *Cell Reports* 19(6):1189-1201, Cell Press, United States (May 2017).
Gatenby, R., and Brown, J., "The Evolution and Ecology of Resistance in Cancer Therapy," *Cold Spring Harbor Perspectives in Medicine* (Jul. 14, 2017).
GenBank, "Programmed cell death 1 ligand 1," Accession No. Q9NZQ7, accessed at https://www.ncbi.nlm.nih.gov/protein/Q9NZQ7 on Sep. 16, 2020, 8 pages.
GenBank, "Human hPD-1 (hPD-1) mRNA, complete cds," Accession No. U64863, accessed at https://www.ncbi.nlm.nih.gov/nuccore/U64863 on Sep. 15, 2020, 3 pages.
Goodman, A.M., et al., "Tumor mutational burden as an independent predictor of response to immunotherapy in diverse cancers," *Molecular Cancer Therapeutics* 16(11):2598-2608, American Association for Cancer Research, United States (Nov. 2017).
Gros, A., et al., "Prospective identification of neoantigen-specific lymphocytes in the peripheral blood of melanoma patients," *Nature Medicine* 22(4):433-438, Nature Publishing Group, United Kingdom (Feb. 2016).
Herbst, R.S., et al., "A study of MPDL3280A, an engineered PD-L1 antibody in patients with locally advanced or metastatic tumors," *J Clin Oncol* 31(15_Suppl): Abstract 3000, American Society of Clinical Oncology, United States (2013).
Herbst, R.S., et al., "Predictive correlates of response to the anti-PD-L1 antibody MPDL3280A in cancer patients," *Nature* 515(7528):563-567, Nature Publishing Group, United Kingdom (2014).
Hodi, F.S., et al., "Combined nivolumab and ipilimumab versus ipilimumab alone in patients with advanced melanoma: 2-year overall survival outcomes in a multicentre, randomised, controlled, phase 2 trial," *The Lancet Oncology* 17(11):1558-1568, Lancet Publishing Group, United Kingdom (Nov. 2016).
Huang, A.C., et al., "T-cell invigoration to tumour burden ratio associated with anti-PD-1 response," *Nature* 545(7652):60-65, Nature Publishing Group, United Kingdom (Apr. 2017).
Hui, R., et al., "Pembrolizumab as first-line therapy for patients with PD-L1-positive advanced non-small cell lung cancer: a phase 1 trial," *Annals of Oncology* 28(4):874-881, Elsevier Ltd., United Kingdom (Apr. 2017).
International Search Report and Written Opinion for Application No. PCT/US2018/044168, dated Nov. 22, 2018, European Patent Office, Netherlands, 9 pages.
Jamal-Hanjani, M., et al., "Translational implications of tumor heterogeneity," *Clin Cancer Res* 21(6):1258-1266, American Association for Cancer Research Inc., United States (2015).
Kamphorst, A.O., et al., "Proliferation of PD-1+ CD8 T cells in peripheral blood after PD-1-targeted therapy in lung cancer patients," *Proc Natl Acad Sci USA* 114(19):4993-4998, National Academy of Sciences, United States (Apr. 2017).
Khleif, S.N., et al., "MEDI4736, an anti-PD-L1 antibody with modified Fc domain: preclinical evaluation and early clinical results from a phase 1 study in patients with advanced solid tumors," *European Journal of Cancer* 49(Suppl. 2):S161, Abstract 802, 17th European Cancer Conference, Sep. 27-Oct. 1, 2013, Elsevier Inc., Netherlands (2013).
Klebanoff, C.A., et al., "Central memory self/tumor-reactive CD8+ T cells confer superior antitumor immunity compared with effector memory T cells," *Proc Natl Acad Sci USA* 102(27):9571-9576, National Academy of Sciences, United States (2005).
Krieg, C., et al., "High-dimensional single-cell analysis predicts response to anti-PD-1 immunotherapy," *Nature Medicine* 24(2):144-153, Nature Publishing Group, United Kingdom (Jan. 2018).
Manjarrez-Orduno, N., et al., "Circulating T Cell Subpopulations Correlate With Immune Responses at the Tumor Site and Clinical Response to PD1 Inhibition in Non-Small Cell Lung Cancer," *Frontiers in Immunology* 9:1613, Frontiers Media S.A., Switzerland (Aug. 2018).
Manjarrez-Orduno, N., et al., "A systemic lupus erythematosus endophenotype characterized by increased CD8 cytotoxic signature associates with renal involvement," *ImmunoHorizons* 1(7):124-32, American Association of Immunologists Inc., United States (Sep. 2017).
Mcgranahan, N., et al., "Clonal neoantigens elicit T cell immunoreactivity and sensitivity to immune checkpoint blockade," *Science* 351(6280):1463-1469, American Association for the Advancement of Science, United States (Mar. 2016).
Purroy, N., et al., "Coevolution of Leukemia and Host Immune Cells in Chronic Lymphocytic Leukemia," *Cold Spring Harbor Perspectives in Medicine* 7(4):a026740, Cold Spring Harbor Laboratory Press, United States (Jan. 2017).
Qiu, P., et al., "Extracting a cellular hierarchy from high-dimensional cytometry data with SPADE," *Nat Biotech* 29(10):886-91, Nature Publishing Group, United Kingdom (2011).
Sjoblom, T., et al., "The consensus coding sequences of human breast and colorectal cancers," *Science* 314(5797):268-274, American Association for the Advancement of Science, United States (2006).
Snyder, A., et al., "Genetic Basis for Clinical Response to CTLA-4 Blockade in Melanoma," *New England Journal of Medicine* 371(23):2189-99, Massachusetts Medical Society, United States (2014).
Spranger, S., et al., "Melanoma-intrinsic beta-catenin signalling prevents anti-tumour immunity," *Nature* 523:231-235, Nature Publishing Group, United Kingdom (2015).
Subrahmanyam, P.B., et al., "Distinct predictive biomarker candidates for response to anti-CTLA-4 and anti-PD-1 immunotherapy in melanoma patients," *Journal for Immunotherapy of Cancer* 6(1): 18, BioMed Central Ltd., United Kingdom (Mar. 2018).

(56) References Cited

OTHER PUBLICATIONS

Takeuchi, Y., et al., "Clinical response to PD-1 blockade correlates with a sub-fraction of peripheral central memory CD4+ T cells in patients with malignant melanoma," *International Immunology* 30(1):13-22, Oxford University Press, United Kingdom (Dec. 2017).

Taube, J.M., et al., "Colocalization of Inflammatory Response with B7-H1 Expression in Human Melanocytic Lesions Supports an Adaptive Resistance Mechanism of Immune Escape," *Science Translational Medicine* 4(127): 127ra37, American Association for the Advancement of Science, United States (2012).

Tietze, J., et al., "The proportion of circulating CD45RO+CD8+ memory T cells is correlated with clinical response in melanoma patients treated with ipilimumab," *European Journal of Cancer* 75:268-279, Elsevier Ltd., Netherlands (Apr. 2017).

Vogelstein, B., et al., "Cancer genome landscapes," *Science* 339(6127):1546-1558, American Association for the Advancement of Science, United States (2013).

Wang, C., et al., "In Vitro Characterization of the Anti-PD-1 Antibody Nivolumab, BMS- 936558, and In Vivo Toxicology in Non-Human Primates," *Cancer Immunology Research* 2(9):846-56, American Association for Cancer Research Inc., United States (2014).

Wherry, E.J., et al., "Lineage relationship and protective immunity of memory CD8 T cell subsets," *Nature Immunology* 4(3):225-34, Nature Publishing Group, United Kingdom (2003).

Yan, Y., et al., "CX3CR1 identifies PD-1 therapy-responsive CD8+ T cells that withstand chemotherapy during cancer chemoimmunotherapy," *JCI Insight* 3(8):e97828, The American Society for Clinical Investigation, United States (Apr. 2018).

Yap, T.A., et al., "Intratumor Heterogeneity: Seeing the Wood for the Trees," *Science Translational Medicine* 4(127): 127ps10, American Association for the Advancement of Science, United States (2012).

National Cancer Institute, "Pembrolizumab," Cancer.gov, accessed at www.cancer.gov/drugdictionary?cdrid=695789 on Sep. 16, 2020, 1 page.

National Cancer Institute, "Anti-PD-1 fusion protein AMP-224," Cancer.gov, accessed at www.cancer.gov/publications/dictionaries/cancer-drug?cdrid=700595 on Sep. 16, 2020, 1 page.

Stemke, A., et al., "Dissertation: Immunity with tumor antigen-specific T cells in ret transgenic mouse melanoma model," Ruperto-Carola University of Heidelberg, Jul. 23, 2013, pp. 1-105.

* cited by examiner

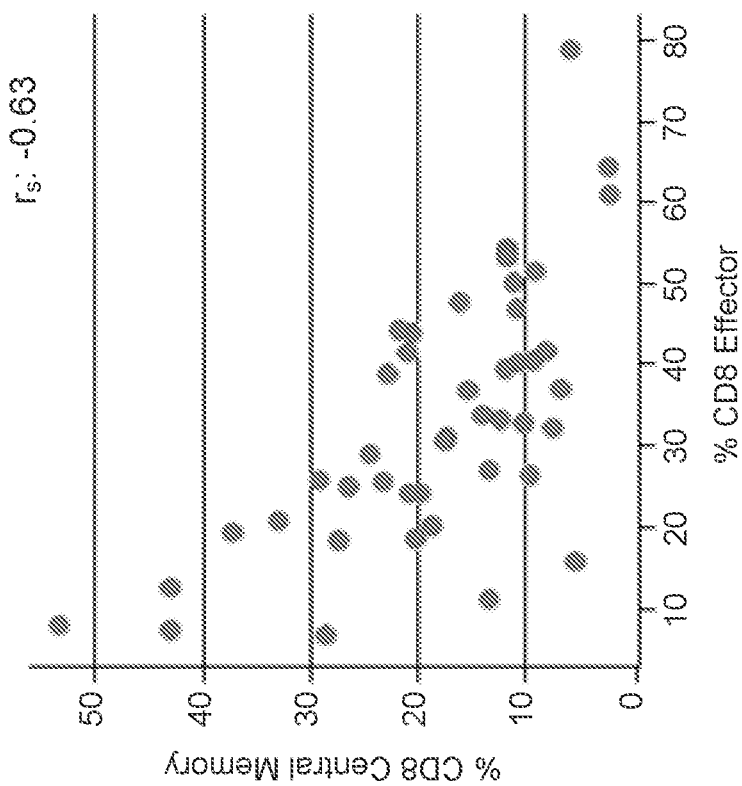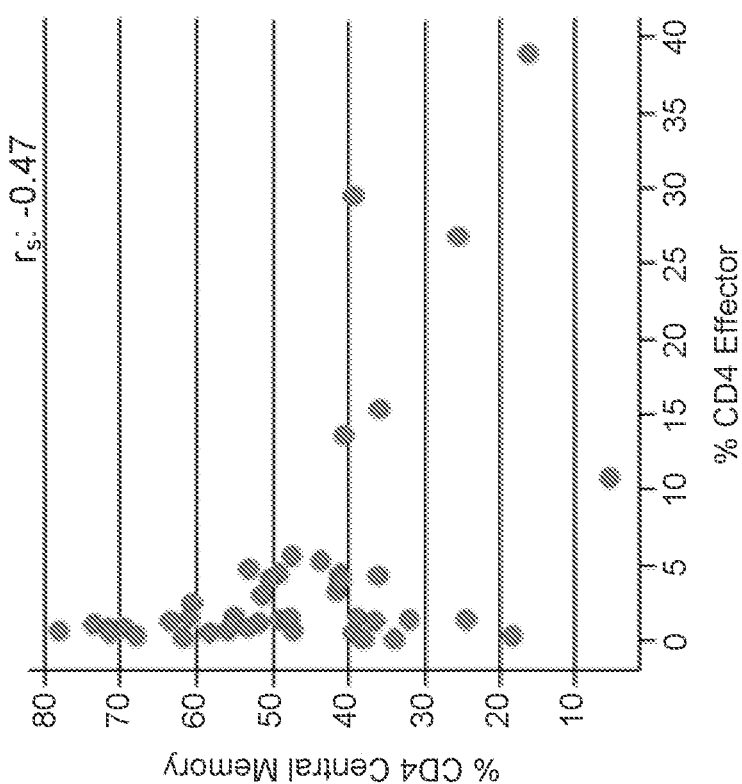
FIG. 4B

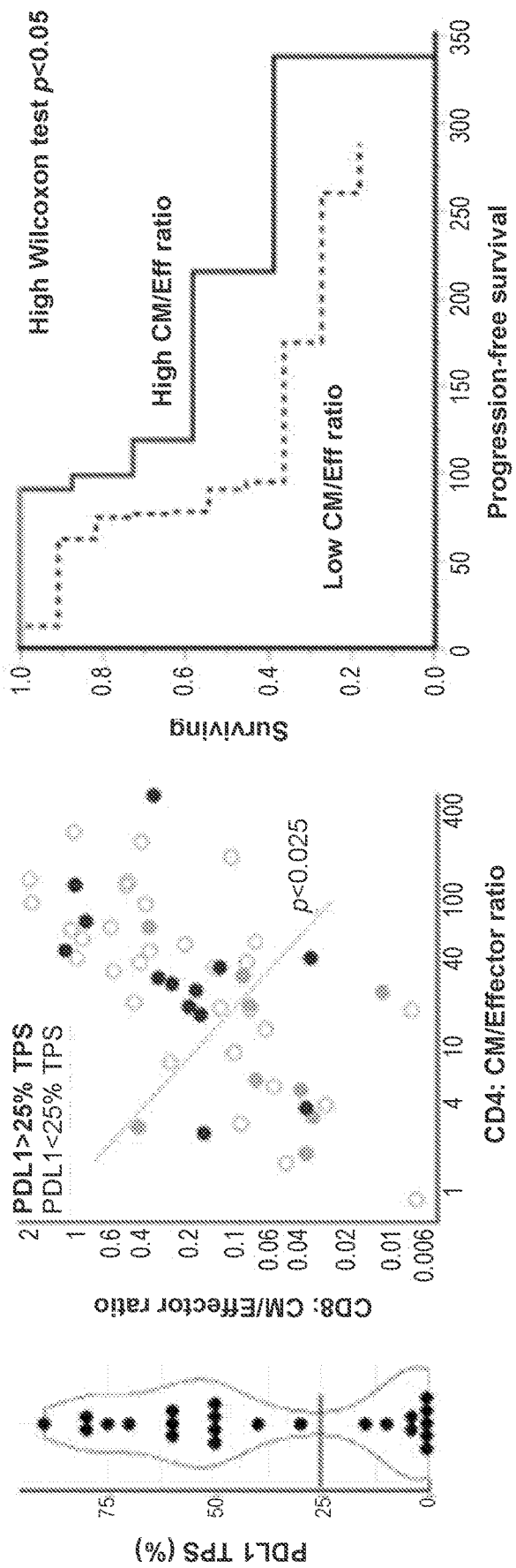

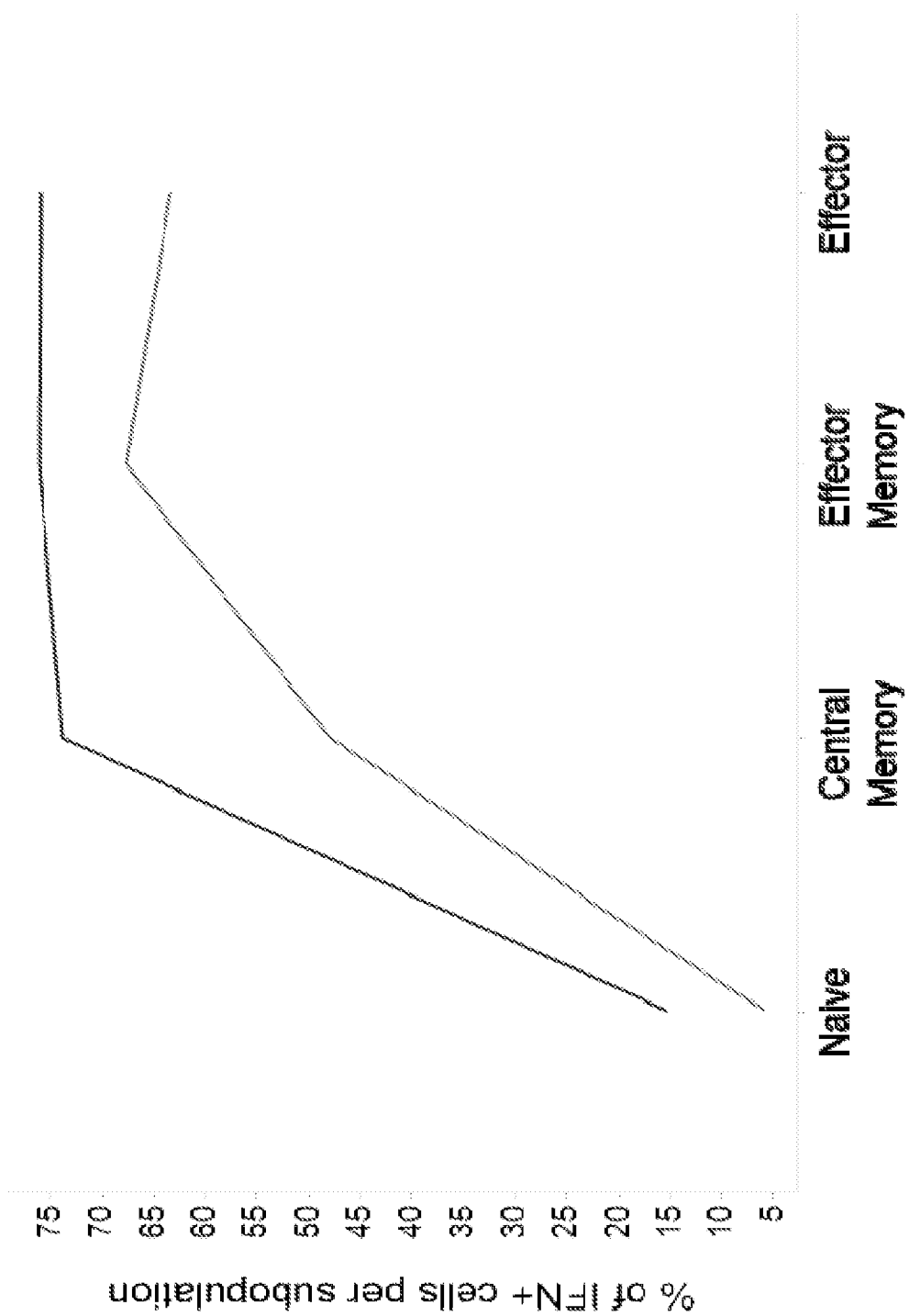

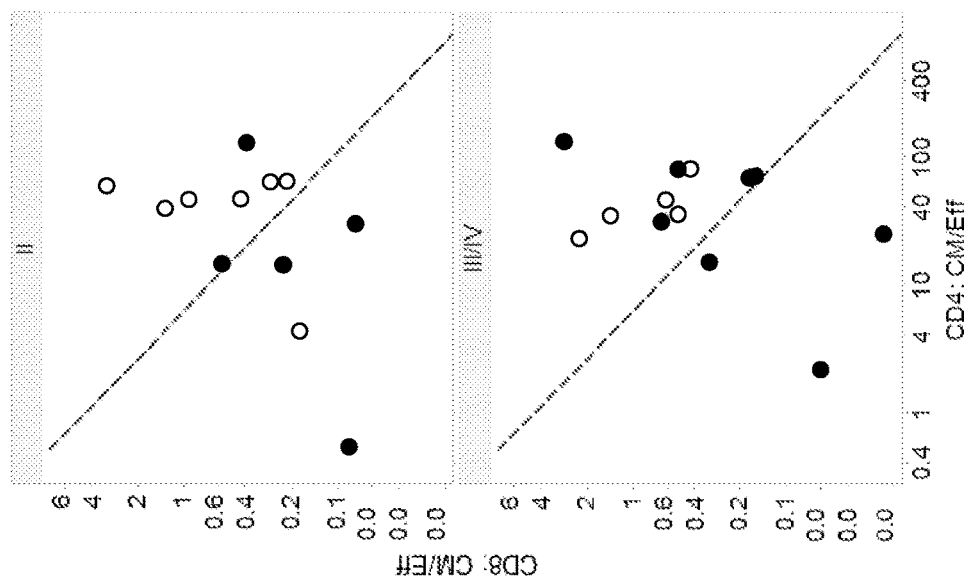
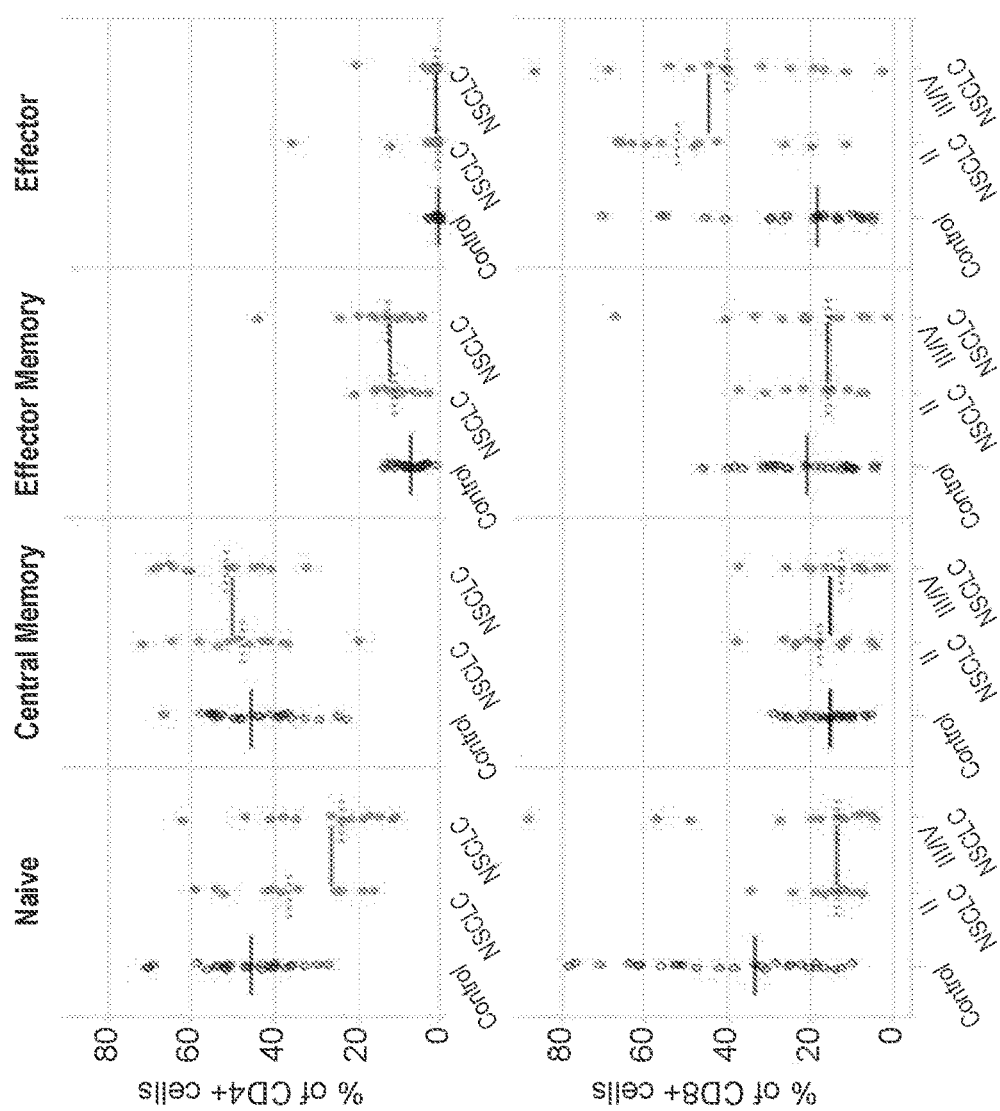
FIG. 11A
FIG. 11B

PREDICTIVE PERIPHERAL BLOOD BIOMARKER FOR CHECKPOINT INHIBITORS

REFERENCE TO EARLIER FILED APPLICATIONS

The present application claims benefit to U.S. Provisional Application No. 62/538,509, filed Jul. 28, 2017, U.S. Provisional Application No. 62/582,166, filed Nov. 6, 2017, and U.S. Provisional Application No. 62/691,556, filed Jun. 28, 2018, which are incorporated herein by reference in their entireties.

FIELD OF THE INVENTION

This invention relates to methods for treating tumors comprising administering to the subject an anti-Programmed Death-1 (PD-1) antibody or an anti-PD-1 ligand 1 (anti-PD-L1) antibody.

BACKGROUND

Human cancers harbor numerous genetic and epigenetic alterations, generating neoantigens potentially recognizable by the immune system (Sjoblom et al. (2006) Science 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Programmed Cell Death Protein 1 (PD-1) is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down-regulate T cell activation and cytokine secretion upon binding to PD-1.

Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56).

A clear need exists for effective agents for patients who have progressed on one or more lines of targeted therapy, as well as for therapies that extend survival for longer periods beyond the current standard treatments. Newer approaches involving immunotherapy, especially blockade of immune checkpoints including the CTLA-4, PD-1, and PD-L1 inhibitory pathways, have recently shown promise (Creelan et al. (2014) *Cancer Control* 21(1):80-89). However, a need remains to identify patients that may be more responsive to immunotherapy, in particular to identify patients that are more likely to respond to an anti-PD-1 or anti-PD-L1 antibody therapy.

SUMMARY

Described herein is the finding that circulating T cell subpopulations, more specifically circulating central memory to effector T cell ratios, correlate with immune inflammatory signatures at the tumor site in melanoma and non-squamous non-small cell lung cancer.

Checkpoint inhibitors have transformed cancer therapy, although outcomes can be variable. Response to anti-PD1 therapies depends in part on tumor type and characteristics, particularly its mutation burden, as well as pre-existing antitumor immunity. These parameters may constitute the basis for patient stratification strategies for several immuno-oncology therapies. Described herein is the characterization of the relationship between the local immune environment at the tumor site and peripheral immunity in melanoma and non-squamous non-small cell lung cancer.

As described in the Examples, distinct circulating T cell maturation patterns that distinguish between control samples and those belonging to patients with the studied tumors were observed. Patients with melanoma and non-squamous lung cancer who have an inflammatory milieu in the tumor as determined by inflammatory signature score have particular T cell profiles that correlate with local inflammation at the tumor site.

Characterization of peripheral immunity, as it relates to the inflammatory immune status in the tumor is described herein. Approaches to measure the immune response which are more easily accessible compared to tumor biopsies are described.

The present disclosure provides a method of determining the existence of an inflammatory milieu in a tumor of a human subject having cancer, comprising determining the level of circulating central memory T ("TCM") cells and the level of circulating T effector memory ("Teff") cells in the subject, wherein a higher ratio of circulating TCM cells to circulating Teff cells ("TCM:Teff") in the subject relative to that in a human subject who has a tumor that does not have an inflammatory milieu indicates that the tumor milieu is inflamed.

Also provided is a method of determining the existence of an inflammatory milieu in a tumor of a human subject having cancer, comprising determining the level of circulating TCM cells and the level of circulating Teff cells in the subject, wherein a ratio of circulating TCM cells to circulating Teff cells ("TCM:Teff") that is similar to or higher than that in the top 90% (i.e., any values except the lower 10%) of healthy subjects (or controls) indicates that the tumor milieu is inflamed.

The disclosure also provides a method of determining the likelihood of response of a human subject having cancer to a checkpoint inhibitor, comprising determining the level of circulating TCM cells and the level of circulating Teff cells in the subject, wherein a higher ratio of circulating TCM cells to circulating Teff cells ("TCM:Teff") in the subject relative to that in a human subject who has a tumor that does not have an inflammatory milieu indicates that the subject is likely to respond to a checkpoint inhibitor.

Also provided is a method of determining the likelihood of response of a human subject having cancer to a checkpoint inhibitor, comprising determining the level of circulating TCM cells and the level of circulating Teff cells in the subject, wherein a ratio of circulating TCM cells to circulating Teff cells ("TCM:Teff") that is similar to or higher than that in the top 90% of healthy subjects indicates that the subject is likely to respond to a checkpoint inhibitor.

In some aspects of the methods disclosed above, the TCM cells and the Teff cells are CD4+ TCM and CD4+ Teff cells, respectively. In some aspects, the TCM cells and the Teff cells are CD8+ TCM and CD8+ Teff cells, respectively. In some aspects, the methods disclosed above comprise determining the level of circulating CD4+ TCM cells, circulating CD8+ TCM, circulating CD4+ Teff cells, and circulating CD8+ Teff cells, wherein both (i) a higher ratio of circulating CD4+ TCM cells to circulating CD4 Teff ("CD4+ TMC:CD4+ Teff") cells and (ii) a higher ratio of circulating CD8+ TCM cells to circulating CD8 Teff ("CD8+ TMC:CD8+ Teff") cells relative to those, respectively, in a human subject who has a tumor that does not have an inflammatory milieu, indicates that the tumor milieu is inflamed.

In some aspects, the methods disclosed herein comprise determining the level of circulating CD4+ TCM cells, circulating CD8+ TCM, circulating CD4+ Teff cells, and circulating CD8+ Teff cells, wherein both (i) a ratio of circulating CD4+ TCM cells to circulating CD4 Teff cells ("CD4+ TMC:CD4+ Teff") and (ii) a ratio of circulating CD8+ TCM cells to circulating CD8 Teff cells ("CD8+ TMC:CD8+ Teff") that is similar to or higher than that, respectively, in the top 90% of healthy subjects indicates that the tumor milieu is inflamed.

In some aspects, the methods disclosed herein comprise determining the level of circulating CD4+ TCM cells, circulating CD8+ TCM, circulating CD4+ Teff cells, and circulating CD8+ Teff cells, wherein both (i) a higher ratio of circulating CD4+ TCM cells to circulating CD4 Teff ("CD4+ TMC:CD4+ Teff") cells and (ii) a higher ratio of circulating CD8+ TCM cells to circulating CD8 Teff ("CD8+ TMC:CD8+ Teff") cells relative to those, respectively, in a human subject who has a tumor that does not have an inflammatory milieu, indicates that the subject is likely to respond to a checkpoint inhibitor.

In some aspects, the methods disclosed herein comprise determining the level of circulating CD4+ TCM cells, circulating CD8+ TCM, circulating CD4+ Teff cells, and circulating CD8+ Teff cells, wherein both (i) a ratio of circulating CD4+ TCM cells to circulating CD4 Teff ("CD4+ TMC:CD4+ Teff") cells and (ii) a ratio of circulating CD8+ TCM cells to circulating CD8 Teff ("CD8+ TMC:CD8+ Teff") cells that is similar to or higher than that, respectively, in the top 90% of healthy subjects indicates that the subject is likely to respond to a checkpoint inhibitor.

In some aspects, the TCM cells are CCR7+ and CD45RA−. In some aspects, the Teff cells are CCR7− and CD45RA+. In some aspects, the checkpoint inhibitor is a PD-1/PD-L1 axis antagonist. In some aspects, the checkpoint inhibitor is a PD-1 antagonist. In some aspects, the PD-1 antagonist is a PD-1 antibody. In some aspects, the PD-1 antibody is nivolumab. In some aspects, the PD-1 antibody is pembrolizumab, PDR001, REGN2810, AMP-514 (MEDI0608) or BGB-A317.

In some aspects, the checkpoint inhibitor is a PD-L1 antagonist. In some aspects, the PD-L1 antagonist is a PD-L1 antibody. In some aspects, the PD-L1 antibody is atezolizumab, durvalumab or avelumab. In some aspects, the checkpoint inhibitor is an antagonist of CTLA-4, LAG-3, TIM3, CEACAM-1, BTLA, CD69, TIGIT, CD113, GPR56, VISTA, 2B4, CD48, GARP, CD73, PD1H, LAIR1, TIM-1,TIM-4, CD39, CSF-1R or IDO.

The present disclosure also provides a method of treating a subject having cancer, comprising administering a checkpoint inhibitor to a subject having a higher ratio of circulating TCM cells to circulating Teff cells ("TCM:Teff") relative to that in a human subject who has a tumor that does not have an inflammatory milieu indicates that the tumor milieu is inflamed.

Also provided is a method of treating a subject having cancer, comprising administering a checkpoint inhibitor to a subject having a ratio of circulating TCM cells to circulating Teff cells ("TCM:Teff") that is similar to or higher than that in the top 90% (i.e., any values except the lower 10%) of healthy subjects. The present disclosure also provides method of treating a subject having cancer, comprising (i) determining the level of circulating TCM cells and the level of circulating Teff cells in a subject having cancer, and if the subject has a higher ratio of circulating TCM cells to circulating Teff cells ("TCM:Teff") relative to that in a human subject who has a tumor that does not have an inflammatory milieu, (ii) administering to the subject a checkpoint inhibitor.

Also provided is a method of treating a subject having cancer, comprising (i) determining the level of circulating TCM cells and the level of circulating Teff cells in the subject, and if the subject has a ratio of circulating TCM cells to circulating Teff cells ("TCM:Teff") that is similar to or higher than that in the top 90% (i.e., any values except the lower 10%) of healthy subjects, (ii) administering to the subject a checkpoint inhibitor. In some aspects, the TCM cells and the Teff cells are CD4+ TCM and CD4+ Teff cells, respectively. In some aspects, the TCM cells and the Teff cells are CD8+ TCM and CD8+ Teff cells, respectively.

Also provided is a method of treating a subject having cancer, comprising administering a checkpoint inhibitor to a subject having both (i) a higher ratio of circulating CD4+ TCM cells to circulating CD4 Teff ("CD4+ TMC:CD4+ Teff") cells and (ii) a higher ratio of circulating CD8+ TCM cells to circulating CD8 Teff ("CD8+ TMC:CD8+ Teff") cells relative to those, respectively, in a human subject who has a tumor that does not have an inflammatory milieu.

The present disclosure also provides a method of treating a subject having cancer, comprising administering a checkpoint inhibitor to a subject having both (i) a ratio of circulating CD4+ TCM cells to circulating CD4 Teff ("CD4+ TMC:CD4+ Teff") cells and (ii) a ratio of circulating CD8+ TCM cells to circulating CD8 Teff ("CD8+ TMC:CD8+ Teff") cells that are similar to or higher than those, respectively, in the top 90% of healthy subjects. Also provided is a method of treating a subject having cancer, comprising (1) determining the level of circulating CD4+ TCM cells, circulating CD8+ TCM, circulating CD4+ Teff cells, and circulating CD8+ Teff cells in a subject having cancer, and if the subject has both (i) a higher ratio of circulating CD4+ TCM cells to circulating CD4 Teff ("CD4+ TMC:CD4+ Teff") cells and (ii) a higher ratio of circulating CD8+ TCM cells to circulating CD8 Teff ("CD8+ TMC:CD8+ Teff") cells relative to those, respectively, in a human subject who has a tumor that does not have an inflammatory milieu, (2) administering to the subject a checkpoint inhibitor. Also provided is a method of treating a subject having cancer, comprising (1) determining the level of circulating CD4+ TCM cells, circulating CD8+ TCM, circulating CD4+ Teff cells, and circulating CD8+ Teff cells in a subject having cancer, and if the subject has both (i) a ratio of circulating CD4+ TCM cells to circulating CD4 Teff ("CD4+ TMC:CD4+ Teff") cells and (ii) a ratio of circulating CD8+ TCM cells to circulating CD8 Teff ("CD8+ TMC:CD8+ Teff") cells that are similar to or higher than those, respectively, in the top 90% of healthy subjects, (2) administering to the subject a checkpoint inhibitor. In some aspects, the TCM cells are CCR7+ and CD45RA−. In some aspects, the Teff cells are CCR7− and CD45RA+. In some aspects, the checkpoint inhibitor is a PD-1/PD-L1 axis antagonist. In some aspects, the checkpoint inhibitor is a PD-1 antagonist. In some aspects, the PD-1 antagonist is a PD-1 antibody. In some aspects, the PD-1 antibody is nivolumab. In some aspects, the PD-1 antibody is pembrolizumab, PDR001, REGN2810, AMP-514 (MEDI0608) or BGB-A317. In some aspects, the checkpoint inhibitor is a PD-L1 antagonist. In some aspects, the PD-L1 antagonist is a PD-L1 antibody. In some aspects, the PD-L1 antibody is atezolizumab, durvalumab or avelumab. In some aspects, the checkpoint inhibitor is an antagonist of CTLA-4, LAG-3, TIM3, CEACAM-1, BTLA, CD69, TIGIT, CD113, GPR56, VISTA, 2B4, CD48, GARP, CD73, PD1H, LAIR1, TIM-1,TIM-4, CD39, CSF-1R or DO. In some aspects, the cancer or tumor is melanoma, lung cancer or kidney cancer. In some aspects, the cancer is NSCLC.

In some aspects, the methods disclosed above further comprise determining the tumor mutational burden (TMB) in a tumor of the subject. In some aspects, if the tumor mutational burden (TMB) is high ($\geq 10$ mutations/megabase), an immunotherapy that stimulates the immune system, such as a checkpoint inhibitor, is administered to the subject.

The present disclosure also provides a method of treating a subject having cancer, comprising administering a checkpoint inhibitor to a subject having (i) a higher ratio of circulating TCM cells to circulating Teff cells ("TCM:Teff") relative to that in a human subject who has a tumor that does not have an inflammatory milieu; and (ii) a high TMB. Also provided is a method of treating a subject having cancer, comprising administering a checkpoint inhibitor to a subject having (i) a ratio of circulating TCM cells to circulating Teff cells ("TCM:Teff") that is similar to or higher than that in the top 90% (i.e., any values except the lower 10%) of healthy subjects and (ii) a high TMB. Also provided is a method of treating a subject having cancer, comprising (i) determining the level of circulating TCM cells and the level of circulating Teff cells in a subject having cancer, and if the subject has a higher ratio of circulating TCM cells to circulating Teff cells ("TCM:Teff") relative to that in a human subject who has a tumor that does not have an inflammatory milieu, and (ii) determining the TMB, and if the TMB is high, then administering to the subject a checkpoint inhibitor.

Also provided is a method of treating a subject having cancer, comprising (i) determining the level of circulating TCM cells and the level of circulating Teff cells in the subject, and if the subject has a ratio of circulating TCM cells to circulating Teff cells ("TCM:Teff") that is similar to or higher than that in the top 90% (i.e., any values except the lower 10%) of healthy subjects, and (ii) determining the TMB, and if the TMB is high, then administering to the subject a checkpoint inhibitor.

In some aspects, the methods disclosed above further comprise determining the level of PD-L1 in a tumor of the subject. In some aspects, an immunotherapy, such as with a checkpoint inhibitor, is only administered to the subject if the PD-L1 level is $\geq 1\%$, $\geq 5\%$ or $\geq 10\%$. For example, an immunotherapy, such as with a checkpoint inhibitor, is only administered to the subject if the PD-L1 level is $\geq 1\%$, $\geq 5\%$ or $\geq 10\%$ in a tumor of the subject and if the TCM:Teff ratio is high, as further described herein. In some embodiments, an immunotherapy, such as with a checkpoint inhibitor, is only administered to a subject having cancer if the PD-L1 level is $\geq 1\%$, $\geq 5\%$ or $\geq 10\%$ in a tumor of the subject and if the TCM:Teff ratio is high, as further described herein, and TMB is high.

The present disclosure provides a method of determining the existence of an inflammatory milieu in a tumor of a human subject having cancer, comprising determining the level of circulating central memory T cells ("TCM level") cells and the level of circulating T effector memory cells ("Teff level") in the subject, wherein (a) a ratio of circulating TCM level to Teff level ("TCM:Teff ratio") in the subject that is higher relative to that in a human subject who has a tumor that does not have an inflammatory milieu; and/or, (b) a TCM:Teff ratio in the subject that is higher or similar to that in the top 90% of healthy subjects (or controls), indicates that the tumor milieu is inflamed.

The present disclosure also provides a method of determining the likelihood of response of a human subject having cancer to a checkpoint inhibitor, comprising determining TCM level and Teff level in the subject, wherein (i) a TCM:Teff ratio in the subject that is higher relative to that in a human subject who has a tumor that does not have an inflammatory milieu; and/or, (ii) a TCM:Teff ratio in the subject that is similar to or higher than that in the top 90% of healthy subjects, indicates that the subject is likely to respond to a checkpoint inhibitor.

Also provided is method of treating a subject having cancer, comprising administering a checkpoint inhibitor to a subject having (a) (i) a TCM:Teff ratio that is higher relative to that in a human subject who has a tumor that does not have an inflammatory milieu; and/or, (ii) a TCM:Teff ratio that is similar to or higher than that in the top 90% of healthy subjects; or, (b) (i) a higher ratio of circulating CD4+ TCM cells to circulating CD4 Teff ("CD4+ TMC:CD4+ Teff") cells and (ii) a higher ratio of circulating CD8+ TCM cells to circulating CD8 Teff ("CD8+ TMC:CD8+ Teff") cells relative to those, respectively, in a human subject who has a tumor that does not have an inflammatory milieu; or, (c) (i) a CD4+ TMC:CD4+ Teff and (ii) a CD8+ TMC:CD8+ Teff that are similar to or higher than those, respectively, in the top 90% of healthy subjects; or, (d) (i) a TCM:Teff ratio in the subject that is higher relative to that in a human subject who has a tumor that does not have an inflammatory milieu; and (ii) a tumor mutational burden ("TMB")$\geq 10$ mutations/megabase; or, (e) (i) a TCM:Teff ratio in the subject that is similar to or higher than that in the top 90% of healthy subjects and (ii) a TMB$\geq 10$ mutations/megabase.

Also provided is a method of treating a subject having cancer comprising,
(a) (i) determining the TCM and Teff levels in the subject, and (ii) administering a checkpoint inhibitor to the subject if the subject has a higher TCM:Teff ratio relative to that in a human subject who has a tumor that does not have an inflammatory milieu; or,
(b) (i) determining the TCM level and Teff levels in the subject, and (ii) administering a checkpoint inhibitor to the subject if the subject has a TCM:Teff ratio that is similar to or higher than that in the top 90% of healthy subjects; or,
(c) (i) determining the CD4+ and CD8+ TCM level, and the CD4+ and CD8+ Teff level in the subject, and (ii) administering a checkpoint inhibitor to the subject if the subject has both (A) a higher CD4+ TMC:CD4+ Teff and (B) a higher CD8+ TMC:CD8+ Teff relative to those, respectively, in a human subject who has a tumor that does not have an inflammatory milieu; or,
(d) (i) determining the CD4+ and CD8+ TCM level, and the CD4+ and CD8+ Teff level in the subject, and (ii) administering a checkpoint inhibitor to the subject if both CD4+ TMC:CD4+ Teff and CD8+ TMC:CD8+ Teff are similar to or higher than those, respectively, in the top 90% of healthy subjects; or,
(e) (i) determining the TCM and Teff levels in the subject, (ii) determining the TMB, and (iii) administering a checkpoint inhibitor to the subject if (A) the subject has a TCM:Teff that is higher than that in a human subject who has a tumor that does not have an inflammatory milieu, and (B) the TMB is ≥10 mutations/megabase; or, (f) (i) determining the TCM and Teff levels in the subject, (ii) determining the TMB, and (iii) administering a checkpoint inhibitor to the subject if (A) the subject has a TCM:Teff that is similar to or higher than that in the top 90% of healthy subjects, and (B) the TMB is ≥10 mutations/megabase.

In some aspects, the method provided herein further comprise determining the level of PD-L1 in a tumor of the subject. In some aspects, the checkpoint inhibitor is only administered to the subject if PD-L1 level is ≥1% or ≥5%. In some aspects, (i) the TCM cells are CD4+ TCM cells and the Teff cells are CD4+ Teff cells; or (ii) the TCM cells are CD8+ TCM cells and the Teff cells are CD8+ Teff cells; or, (iii) the TCM cells are CD4+ TCM cells and CD8+ TCM cells, and the Teff cells are CD4+ Teff cells and CD8+ Teff cells. In some aspects, the TCM cells are CCR7+ and CD45RA−. In some aspects, the Teff cells are CCR7− and CD45RA+. In some aspects, the checkpoint inhibitor comprises a PD-1 antibody. In some aspects, the PD-1 antibody is selected from the group consisting of nivolumab, pembrolizumab, PDR001, REGN2810, AMP-514 (MEDI0608) and BGB-A317. In some aspects, the checkpoint inhibitor comprises a PD-L1 antibody. In some aspects, the PD-L1 antibody is selected from the group consisting of atezolizumab, durvalumab and avelumab. In some aspects, the checkpoint inhibitor comprises an antagonist of CTLA-4, LAG-3, TIM3, CEACAM-1, BTLA, CD69, TIGIT, CD113, GPR56, VISTA, 2B4, CD48, GARP, CD73, PD1H, LAIR1, TIM-1,TIM-4, CD39, CSF-1R or IDO. In some aspects, the cancer or tumor is a melanoma, a lung cancer such as NSCLC, or kidney cancer.

The present disclosure also provides an in vitro method of determining the existence of an inflammatory milieu in a tumor of a human subject having cancer, comprising determining the level of circulating central memory T cells ("TCM level") cells and the level of circulating T effector memory cells ("Teff level") in a sample obtained from the subject, wherein (a) a ratio of circulating TCM level to Teff level ("TCM:Teff ratio") in the subject that is higher relative to that in a human subject who has a tumor that does not have an inflammatory milieu; and/or, (b) a TCM:Teff ratio in the subject that is higher or similar to that in the top 90% of healthy subjects (or controls), indicates that the tumor milieu is inflamed.

Also provided is an in vitro method of determining the likelihood of response of a human subject having cancer to a checkpoint inhibitor, comprising determining TCM level and Teff level in a sample obtained from the subject, wherein (i) a TCM:Teff ratio in the subject that is higher relative to that in a human subject who has a tumor that does not have an inflammatory milieu; and/or, (ii) a TCM:Teff ratio in the subject that is similar to or higher than that in the top 90% of healthy subjects, indicates that the subject is likely to respond to a checkpoint inhibitor.

Also provided is checkpoint inhibitor for use in the treatment of a subject having cancer, wherein the subject has (a) (i) a TCM:Teff ratio that is higher relative to that in a human subject who has a tumor that does not have an inflammatory milieu; and/or, (ii) a TCM:Teff ratio that is similar to or higher than that in the top 90% of healthy subjects; or, (b) (i) a higher ratio of circulating CD4+ TCM cells to circulating CD4 Teff ("CD4+ TMC:CD4+ Teff") cells and/or (ii) a higher ratio of circulating CD8+ TCM cells to circulating CD8 Teff ("CD8+ TMC:CD8+ Teff") cells relative to those, respectively, in a human subject who has a tumor that does not have an inflammatory milieu; or, (c) (i) a CD4+ TMC:CD4+ Teff and/or (ii) a CD8+ TMC:CD8+ Teff that are similar to or higher than those, respectively, in the top 90% of healthy subjects; or, (d) (i) a TCM:Teff ratio in the subject that is higher relative to that in a human subject who has a tumor that does not have an inflammatory milieu; and (ii) a tumor mutational burden ("TMB")≥10 mutations/megabase; or, (e) (i) a TCM:Teff ratio in the subject that is similar to or higher than that in the top 90% of healthy subjects and (ii) a TMB≥10 mutations/megabase.

The present disclosure also provides a checkpoint inhibitor for use in the treatment of a subject having cancer, wherein the treatment comprises, (a) (i) determining the TCM and Teff levels in the subject, and (ii) administering the checkpoint inhibitor to the subject if the subject has a higher TCM:Teff ratio relative to that in a human subject who has a tumor that does not have an inflammatory milieu; or, (b) (i) determining the TCM level and Teff levels in the subject, and (ii) administering the checkpoint inhibitor to the subject if the subject has a TCM:Teff ratio that is similar to or higher than that in the top 90% of healthy subjects; or, (c) (i) determining the CD4+ and CD8+ TCM level, and the CD4+ and CD8+ Teff level in the subject, and (ii) administering the checkpoint inhibitor to the subject if the subject has both (A) a higher CD4+ TMC:CD4+ Teff and (B) a higher CD8+ TMC:CD8+ Teff relative to those, respectively, in a human subject who has a tumor that does not have an inflammatory milieu; or, (d) (i) determining the CD4+ and CD8+ TCM level, and the CD4+ and CD8+ Teff level in the subject, and (ii) administering the checkpoint inhibitor to the subject if both CD4+ TMC:CD4+ Teff and CD8+ TMC:CD8+ Teff are similar to or higher than those, respectively, in the top 90% of healthy subjects; or, (e) (i) determining the TCM and Teff levels in the subject, (ii) determining the TMB, and (iii) administering the checkpoint inhibitor to the subject if (A) the subject has a TCM:Teff that is higher than that in a human subject who has a tumor that does not have an inflammatory milieu, and (B) the TMB is ≥10 mutations/megabase; or, (f) (i) determining the TCM and Teff levels in the subject, (ii) determining the TMB, and (iii) administering the checkpoint inhibitor to the subject if (A) the subject has a TCM:Teff that is similar to or higher than that in the top 90% of healthy subjects, and (B) the TMB is ≥10 mutations/megabase.

In some aspects of the in vitro methods, or the checkpoint inhibitors for use in the treatment of a subject having cancer disclosed herein, the method or the treatment further comprise determining in vitro the level of PD-L1 in a sample obtained from tumor of the subject. In some aspects, the checkpoint inhibitor the checkpoint inhibitor is only administered to the subject if PD-L1 level is ≥1% or ≥5%.

In some aspects of the in vitro methods, or the checkpoint inhibitors for use in the treatment of a subject having cancer disclosed herein (i) the TCM cells are CD4+ TCM cells and the Teff cells are CD4+ Teff cells; or
(ii) the TCM cells are CD8+ TCM cells and the Teff cells are CD8+ Teff cells; or,
(iii) the TCM cells are CD4+ TCM cells and CD8+ TCM cells, and the Teff cells are CD4+ Teff cells and CD8+ Teff cells.

In some aspects of the in vitro methods, or the checkpoint inhibitors for use in the treatment of a subject having cancer disclosed herein, the TCM cells are CCR7+ and CD45RA−. In some aspects of the in vitro methods, or the checkpoint inhibitors disclosed above, the Teff cells are CCR7− and CD45RA+.

In some aspects of the in vitro methods, or the checkpoint inhibitors for use in the treatment of a subject having cancer disclosed herein, the checkpoint inhibitor comprises a PD-1 antibody. In some aspects of the in vitro methods, or the checkpoint inhibitors for use in the treatment of a subject having cancer disclosed herein, the PD-1 antibody is selected from the group consisting of nivolumab, pembrolizumab, PDR001, REGN2810, AMP-514 (MEDI0608) and BGB-A317.

In some aspects of the in vitro methods, or the checkpoint inhibitors for use in the treatment of a subject having cancer disclosed herein, the checkpoint inhibitor comprises a PD-L1 antibody. In some aspects of the in vitro methods, or the checkpoint inhibitors for use in the treatment of a subject having cancer disclosed herein, the PD-L1 antibody is selected from the group consisting of atezolizumab, durvalumab and avelumab.

In some aspects of the in vitro methods, or the checkpoint inhibitors for use in the treatment of a subject having cancer disclosed herein, the checkpoint inhibitor comprises an antagonist of CTLA-4, LAG-3, TIM3, CEACAM-1, BTLA, CD69, TIGIT, CD113, GPR56, VISTA, 2B4, CD48, GARP, CD73, PD1H, LAIR1, TIM-1,TIM-4, CD39, CSF-1R or IDO. In some aspects of the in vitro methods, or the checkpoint inhibitors for use in the treatment of a subject having cancer disclosed herein, the cancer or tumor is a melanoma, a lung cancer such as NSCLC, or kidney cancer.

BRIEF DESCRIPTION OF THE FIGURES

FIG. 3B), respectively, indicating that circulating CD4+ central memory T cells increase with inflammation score in melanoma patients.

FIG. 4B shows the inverse relationship between the levels of central memory ("Central Mem") T cells and Teff cells ("Effector") in CD4 and CD8 populations of melanoma patients.

FIG. 6A shows a gating strategy to define T cell subpopulations in PBMC. FIG. 6B shows CD4+ and CD8+ T cell subpopulations in PBMC from control, melanoma and NSCLC patients (shown from left to right for each type of cell). (Controls n=27, melanoma n=43, NSCLC n=40; Bonferroni-corrected p-values: *<0.001). Line marks the median.

FIG. 7A shows SPADE-generated maturation profiles of CD8+ T cells for two melanoma samples showing the divergent patterns of T cell subpopulations. Both have a reduction in naïve CD8+ T cells but show an expansion in either CM (solid arrow) or the Eff (open arrow) compartments. eEM: early Effector Memory; EM: Effector Memory. FIG. 7B shows correlation between circulating CM and Eff CD4+ and CD8+ T cells and tumor inflammation state (* p<0.05) (the percentage of non-inflamed and inflamed cells are shown on the left and right, respectively, under each type of cell). FIG. 7C shows correlation between CM/Eff T cell ratios by inflammation state in melanoma and NSCLC. Fisher's exact test p-value for a 0.05 significance level. Dividing line generated based on the 90$^{th}$ percentile of controls.

FIGS. 8A, 8B, 8C and 8D show that high CM/Eff T cell ratios associate with longer PFS in response to nivolumab treatment for NSCLC. FIG. 8A shows peripheral T cell profiles in a second cohort of NSCLC and control samples (Bonferroni-corrected p-values: *<0.001, **<0.0001, line marks the median for subpopulation; control and non small cell lung populations are shown on the left and right, respectively, of each type of cell). FIG. 8B shows the distribution of PDL1 tumor proportion score (TPS) (n=23, the horizontal line marks the cut-off at the antimode: 25% TPS). FIG. 8C shows CM/Eff T cell ratios in the NSCLC cohort coded by PDL1 TPS (Open circles: PDL1 expression not evaluated). CM/Eff T cell ratios high vs. low division line is drawn using the 90$^{th}$ percentile of the control samples. Fischer p-value <0.025. FIG. 8D shows PFS after nivolumab treatment (n=22). (p-value<0.05, median survival by CM/Eff ratio: low, 91 days; high 215 days).

FIG. 10 shows Interferon production by CD8 T cell subpopulations along differentiation in two control samples. PBMC were stimulated with phorbol-12-myristate 13-acetate (81 nM), ionomycin (1.33 μM) in the presence of Brefeldin A (5 μg/ml) (Cell Activation Cocktail; BioLegend) for 5 hours at 37° C. Samples were then stained for CD3 (Clone SK7, BV395), CD4 (SK3, BV496), CD8 (RPA-T8, APC-R700), CD45RO (UCHL1, BV786), and CCR7 (G043H7). Samples were treated with an intracellular fixation and permeabilization kit (BioLegend) following the manufacturer's instructions to stain for IFN-γ (4S.B3, AX488) or an isotype control (MOPC-21, AX488).

FIG. 11A shows the percentage of CD4 and CD8 T cell subpopulations in NSCLC separated by tumor stage (II vs III & IV). The continuous horizontal lines mark the median per each subpopulations, the dotted lines mark the median per subgroup.

FIG. 11B shows CM/Eff T cell ratios evaluated by tumor stage, (II vs III & IV), as described in the text. Chi-squared ns.

DETAILED DESCRIPTION

Figure 1:
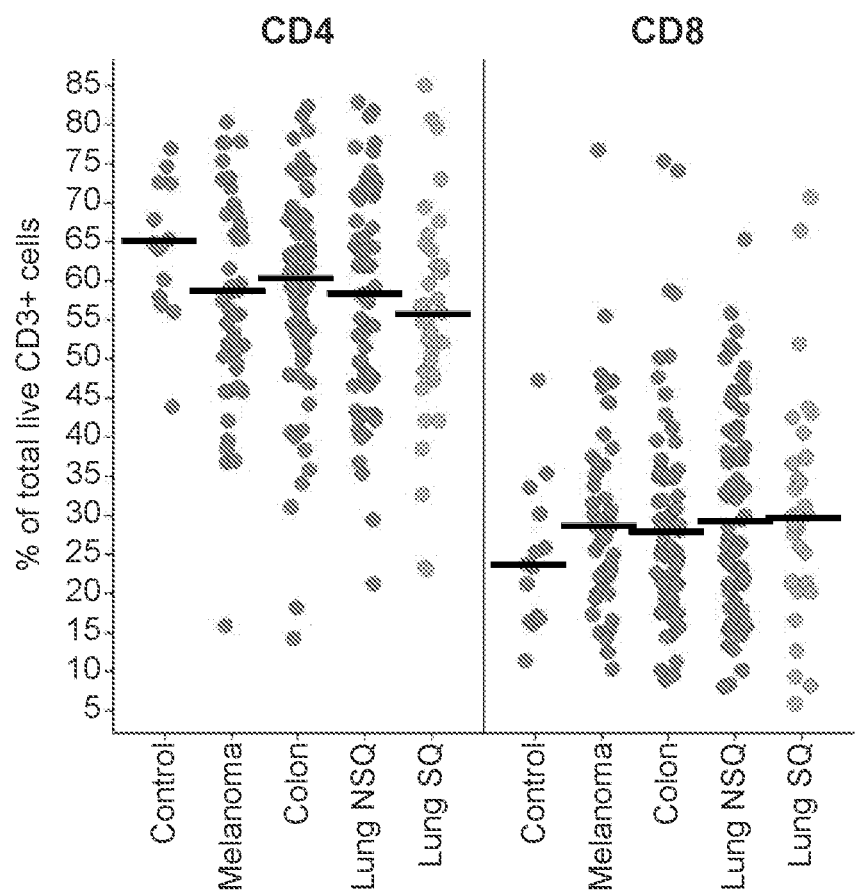
FIG. 1 shows the CD4+ and CD8+ T cells as percentage of total CD3 cells, indicating an expanded CD8+ T cell percentage in most cancer patients relative to healthy subjects. From left to right in each of the CD4 and CD8 graphs are the numbers of cells in healthy subjects ("control"), melanoma patients ("melanoma"), colon cancer patients ("colon"), non-squamous lung cancer patients ("Lung Nsq") and squamous lung cancer patients ("Lung Sq").

The present disclosure relates to methods of determining the existence of an inflammatory milieu in a tumor of a human subject having cancer, comprising determining the level of circulating central memory T ("TCM") cells and the level of circulating T effector memory ("Teff") cells in the subject. The disclosure also provides a method of determining the likelihood of response of a human subject having cancer to a checkpoint inhibitor based on the presence or absence of an inflammatory milieu, wherein a tumor that does not have an inflammatory milieu indicates that the subject is not likely to respond to a checkpoint inhibitor. The disclosure also provides a method of treating a subject having cancer, comprising administering a checkpoint inhibitor to a subject having a higher ratio of circulating TCM cells to circulating Teff cells ("TCM:Teff") relative to that in a human subject who has a tumor that does not have an inflammatory milieu.

TERMS

In order that the present disclosure can be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Routes of administration for the PD-1/PD-L1 antagonist, e.g., anti-PD-1 antibody and/or the anti-PD-L1 antibody, include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some aspects, the combination is administered via a non-parenteral route, in some aspects, orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs can mediate the binding of the immunoglobulin to host tissues or factors, including various cells of the immune system (e.g., effector cells) and the first component (C1q) of the classical complement system.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A mAb is an example of an isolated antibody. MAbs can be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human Abs of the invention can include amino acid residues not encoded by human germline immunoglobulin sequences (e.g., mutations introduced by random or site-specific mutagenesis in vitro or by somatic mutation in vivo). However, the term "human antibody," as used herein, is not intended to include Abs in which CDR sequences derived from the germline of another mammalian species, such as a mouse, have been grafted onto human framework sequences. The terms "human" Abs and "fully human" Abs and are used synonymously.

A "humanized antibody" refers to an antibody in which some, most or all of the amino acids outside the CDR domains of a non-human antibody are replaced with corresponding amino acids derived from human immunoglobulins. In one aspect of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human Ab.

An "anti-antigen" antibody refers to an antibody that binds specifically to the antigen. For example, an anti-PD-1 antibody binds specifically to PD-1.

An "antigen-binding portion" of an antibody (also called an "antigen-binding fragment") refers to one or more fragments of an antibody that retain the ability to bind specifically to the antigen bound by the whole Ab.

A "cancer" refers a broad group of various diseases characterized by the uncontrolled growth of abnormal cells in the body. A "cancer" or "cancer tissue" can include a tumor. Unregulated cell division and growth results in the formation of malignant tumors that invade neighboring tissues and may also metastasize to distant parts of the body through the lymphatic system or bloodstream. Following metastasis, the distal tumors can be said to be "derived from" the original, pre-metastasis tumor. For example, a "tumor derived from" an NSCLC refers to a tumor that is the result of a metastasized NSCLC. Because the distal tumor is derived from the pre-metastasis tumor, the "derived from" tumor can also comprise the pre-metastasis tumor, e.g., a tumor derived from an NSCLC can comprise an NSCLC.

In some aspects, the cancer is colorectal cancer, rectal cancer, colon cancer, lung cancer, melanoma, ovarian cancer, head and neck cancer, or any combination thereof. In certain aspects, the lung cancer is non-small cell lung cancer (NSCLC). In aspects, the NSCLC has a squamous histology. In other aspects, the NSCLC has a nonsquamous histology.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. "Treating a subject having cancer" is understood to mean "treating the cancer in the subject having cancer."

"Immunotherapy" refers to a therapy that stimulates the immune system, e.g., to reject tumors.

"Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or nonhuman animal. The term "nonhuman animal" includes, but is not limited to, vertebrates such as nonhuman primates, sheep, dogs, and rodents such as mice, rats and guinea pigs. In some aspects, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Methods of the Invention

Provided herein are methods for determining whether the immune system of a subject having a tumor is reacting to, or likely to react to, a tumor in the subject, comprising determining the level of certain types of T cells in the blood of the subject. In particular, the present disclosure provide methods of determining the existence of an inflammatory milieu in a tumor of a human subject having cancer, e.g., melanoma, lung cancer or kidney cancer, comprising determining the level of circulating central memory T ("TCM") cells and the level of circulating T effector memory ("Teff") cells in the subject, wherein a higher ratio of circulating TCM cells to circulating Teff cells ("TCM:Teff") in the subject relative to that in a human subject who has a tumor that does not have an inflammatory milieu indicates that the tumor milieu is inflamed. A ratio of circulating TCM cells to circulating Teff cells ("TCM:Teff") that is similar to or higher than that in, e.g., the top 90% (in fact, any values except the lower 10%) of healthy subjects (or controls) indicates that the tumor milieu is inflamed.

In certain aspects, the level of CD4+ and/or CD8+ central memory T cells is measured in a sample obtained from the subject, e.g., a blood sample. Thus, in certain aspects, the level of CD4+ central memory T cells and CD4+ effector T cells are measured, e.g., in the blood of the subject. In certain aspects, the level of CD8+ central memory T cells and CD8+ effector T cells are measured e.g., in the blood of the subject. In certain aspects, the level of CD4+ central memory T cells, CD4+ effector T cells, CD8+ central memory T cells and CD8+ effector T cells are measured e.g., in the blood of the subject. In certain aspects, the ratio of circulating (i.e., present in the blood or peripheral blood) CD4+ central memory T cells to circulating CD4+ effector T cells is determined. In certain aspects, the ratio of circulating CD8+ central memory T cells to circulating CD8+ effector T cells is determined. In certain aspects, the ratio of circulating CD4+ central memory T cells to circulating CD4+ effector T cells is determined and the ratio of circulating CD8+ central memory T cells to circulating CD8+ effector T cells is determined.

As further shown herein, the level of circulating central memory T cells in a human subject having a tumor (cancer) correlates with the presence of an inflammatory milieu in the tumor, and also correlates with a response of the subject to a checkpoint inhibitor. Thus, determining the level of circulating CD4+ and/or CD8+ central memory T cells in a subject having a tumor (cancer) can be used for predicting or determining whether the subject has an inflammatory milieu in a tumor and whether the subject is likely to respond to therapy with a checkpoint inhibitor. Accordingly, the present disclosure provides methods of determining the likelihood of response of a human subject having cancer to a checkpoint inhibitor, comprising determining the level of circulating central memory T cells and the level of circulating Teff cells in the subject, wherein a higher ratio of circulating TCM cells to circulating Teff cells ("TCM:Teff") in the subject relative to that in a human subject who has a tumor that does not have an inflammatory milieu indicates that the subject is likely to respond to a checkpoint inhibitor. In some aspects, the checkpoint inhibitor is an antagonist of CTLA-4, LAG-3, TIM3, CEACAM-1, BTLA, CD69, TIGIT, CD113, GPR56, VISTA, 2B4, CD48, GARP, CD73, PD1H, LAIR1, TIM-1, TIM-4, CD39, CSF-1R or IDO or other protein that inhibits the immune system.

In certain aspects, determining the level of circulating CD4+ central memory T cells and circulating CD4+ effector T cells and/or the level of circulating CD8+ central memory T cells and circulating CD8+ effector T cells in a subject having a tumor (cancer) can be used for predicting or determining whether the subject has an inflammatory milieu in a tumor and whether the subject is likely to respond to therapy with a checkpoint inhibitor. Thus, the present disclosure also provides methods of determining the likelihood of response of a human subject having cancer to a checkpoint inhibitor, comprising determining the level of circulating central memory T cells and the level of circulating Teff cells in the subject, wherein a ratio of circulating central memory T cells to circulating Teff cells ("TCM:Teff") that is similar to or higher than that in the top 90% of healthy subjects indicates that the subject is likely to respond to a checkpoint inhibitor.

In certain aspect, determining the ratio of circulating CD4+ central memory T cells to circulating CD4+ effector T cells ("CD4+ central memory T cells:effector T cells") and/or the ratio of circulating CD8+ central memory T cells to circulating CD8+ effector T cells ("CD8+ central memory T cells:effector T cells") in a subject having a tumor (cancer) can be used for predicting or determining whether the subject has an inflammatory milieu in a tumor and whether the subject is likely to respond to therapy with a checkpoint inhibitor. In certain aspects, determining the ratio of circulating CD4+ central memory T cells to circulating CD4+ effector T cells ("CD4+ central memory T cells:effector T cells") and the ratio of circulating CD8+ central memory T cells to circulating CD8+ effector T cells ("CD8+ central memory T cells:effector T cells") in a subject having a tumor (cancer) can be used for predicting or determining whether the subject has an inflammatory milieu in a tumor and whether the subject is likely to respond to therapy with a checkpoint inhibitor.

As further shown herein, a high level of circulating CD4+ and/or CD8+ central memory T cells in a subject having a tumor (cancer) correlates with the presence of an inflammatory milieu in a tumor of the subject and the response of the subject to therapy with a checkpoint inhibitor, e.g., a PD-1 antagonist. In certain aspects, the presence of a high level of circulating CD4+ and/or CD8+ central memory T cells in a subject having a tumor (cancer) relative to that in a subject that has a tumor that does not have an inflammatory milieu is predictive of the presence of an inflammatory milieu in a tumor of the subject and of the response of the subject to therapy with a checkpoint inhibitor, e.g., a PD-1 antagonist. In certain aspects, the presence of a high level of circulating CD4+ and/or CD8+ central memory T cells and the presence of low levels of circulating CD4+ and/or CD8+ effector T cells in a subject having a tumor (cancer) relative to the levels, respectively, in a subject that has a tumor that does not have an inflammatory milieu is predictive of the presence of an inflammatory milieu in a tumor of the subject and of the response of the subject to therapy with a checkpoint inhibitor, e.g., a PD-1 antagonist.

A "high level" may be relative (i) to that present in a subject who has a tumor that does not have an inflammatory milieu; (ii) the average level in a group of subjects who have a tumor that does not have an inflammatory milieu, and the difference is statistically significant, or (iii) the level in the top 90%, 80%, 70%, 60%, 50%, 40%, 30%, 20% or 10% of healthy subjects, i.e., subjects having a normal strength immune system.

In certain aspects, the presence of a similar or higher ratio of the level of circulating CD4+ central memory T cells to the level of circulating CD4+ effector T cells in a subject having a tumor (cancer) relative to that in a subject that has (or group of subjects that have) a tumor that does not have an inflammatory milieu is predictive of the presence of an inflammatory milieu in a tumor of the subject and of the response of the subject to therapy with a checkpoint inhibitor, e.g., a PD-1 antagonist. In certain aspects, the presence of a similar or higher ratio of the level of circulating CD8+ central memory T cells to the level of circulating CD8+ effector T cells in a subject having a tumor (cancer) relative to that in a subject that has (or group of subjects that have) a tumor that does not have an inflammatory milieu is predictive of the presence of an inflammatory milieu in a tumor of the subject and of the response of the subject to therapy with a checkpoint inhibitor, e.g., a PD-1 antagonist.

In certain aspects, the presence of a similar or higher ratio of the level of circulating CD4+ central memory T cells to the level of circulating CD4+ effector T cells and a higher ratio of the level of circulating CD8+ central memory T cells to the level of circulating CD8+ effector T cells in a subject having a tumor (cancer) relative to those ratios, respectively, in a subject that has (or group of subjects that have) a tumor that does not have an inflammatory milieu is predictive of the presence of an inflammatory milieu in a tumor of the subject and of the response of the subject to therapy with a checkpoint inhibitor, e.g., a PD-1 antagonist. When comparing to the values in a group of subjects, the comparison may be against the average or median value of the group of subjects, wherein a difference is statistically significant. A higher ratio may be 50%, 100% (2 fold), 3 fold, 4 fold 5 fold or more.

In certain aspects, the presence of a similar or higher ratio of the level of circulating CD4+ central memory T cells to the level of circulating CD4+ effector T cells in a subject having a tumor (cancer) relative to that in healthy subjects (having a healthy immune system) is predictive of the presence of an inflammatory milieu in a tumor of the subject and of the response of the subject to therapy with a checkpoint inhibitor, e.g., a PD-1 antagonist. In certain aspects, the presence of a similar or higher ratio of the level of circulating CD8+ central memory T cells to the level of circulating CD8+ effector T cells in a subject having a tumor (cancer) relative to that in healthy subjects (having a healthy immune system) is predictive of the presence of an inflammatory milieu in a tumor of the subject and of the response of the subject to therapy with a checkpoint inhibitor, e.g., a PD-1 antagonist.

In certain aspects, the presence of a similar or higher ratio of the level of circulating CD4+ central memory T cells to the level of circulating CD4+ effector T cells and a higher ratio of the level of circulating CD8+ central memory T cells to the level of circulating CD8+ effector T cells in a subject having a tumor (cancer) relative to those ratios, respectively, in healthy subjects (having a healthy immune system) is predictive of the presence of an inflammatory milieu in a tumor of the subject and of the response of the subject to therapy with a checkpoint inhibitor, e.g., a PD-1 antagonist. When comparing to the values in a group of healthy subjects, the comparison may be against the average or median value of the group of healthy subjects, wherein a difference is statistically significant.

In certain aspects, the presence of a similar or higher ratio of the level of circulating CD4+ central memory T cells to the level of circulating CD4+ effector T cells in a subject having a tumor (cancer) relative to that in the top 90%, 80%, 70%, 60%, 50%, 40%, 30%, 20% or 10% of healthy subjects is predictive of the presence of an inflammatory milieu in a tumor of the subject and of the response of the subject to therapy with a checkpoint inhibitor, e.g., a PD-1 antagonist. In certain aspects, the presence of a similar or higher ratio of the level of circulating CD8+ central memory T cells to the level of circulating CD8+ effector T cells in a subject having a tumor (cancer) relative to that in the top 90%, 80%, 70%, 60%, 50%, 40%, 30%, 20% or 10% of healthy subjects is predictive of the presence of an inflammatory milieu in a tumor of the subject and of the response of the subject to therapy with a checkpoint inhibitor, e.g., a PD-1 antagonist. In certain aspects, the presence of a similar or higher ratio of the level of circulating CD4+ central memory T cells to the level of circulating CD4+ effector T cells and a higher ratio of the level of circulating CD8+ central memory T cells to the level of circulating CD8+ effector T cells in a subject having a tumor (cancer) relative to those ratios, respectively, in the top 90%, 80%, 70%, 60%, 50%, 40%, 30%, 20% or 10% of healthy subjects is predictive of the presence of an inflammatory milieu in a tumor of the subject and of the response of the subject to therapy with a checkpoint inhibitor, e.g., a PD-1 antagonist.

When comparing to the values in a group of subjects, the comparison may be against the average or median value of the group of subjects, wherein a difference is statistically significant. A level of certain T cells or a ratio of certain T cells in the top 90% of healthy subjects refers to an average or median level or ratio that is found in healthy subjects, except the bottom 10% of subjects who have the lowest level or ratio of all healthy subjects.

In some aspects, the subject is a human patient. In certain aspects, the subject is a chemotherapy-naïve patient (e.g., a patient who has not previously received any chemotherapy). In other aspects, the subject for the present combination therapy has received another cancer therapy (e.g., a chemotherapy), but is resistant or refractory to such another cancer therapy.

In certain aspects, the methods of the present disclosure effectively increase the duration of survival of the subject, e.g., the overall survival of the subject. In some aspects, the methods of the present disclosure increase the progression-free survival of the subject. In certain aspects, the methods of the present disclosure increase the progression-free survival of the subject in comparison to standard-of-care therapies.

In some aspects, the cancer is colorectal cancer, rectal cancer, colon cancer, lung cancer, melanoma, ovarian cancer, head and neck cancer, or any combination thereof. In certain aspects, the subject has received one, two, three, four, five or more prior cancer treatments. In other aspects, the subject is treatment-naïve. In some aspects, the subject has progressed on other cancer treatments. In aspects, the cancer has reoccurred. In some aspects, the cancer is metastatic. In other aspects, the cancer is not metastatic.

In certain aspects, the lung cancer is non-small cell lung cancer (NSCLC). In aspects, the NSCLC has a squamous histology. In other aspects, the NSCLC has a nonsquamous histology. In yet other aspects, the NSCLC has a squamous adenosquamous histology. In further aspects, the NSCLC has a histology that is not otherwise specified. In certain aspects, the malignancy is unresectable. In some aspects, the NSCLC is EGFR mutated.

In some aspects, the head and neck cancer is recurrent or metastatic or recurrent SCCHN (oral cavity, pharynx, larynx). In certain aspects the head and neck cancer is stage III/IV. In some aspects, the cancer has progressed or reoccurred within six months of the last dose of platinum therapy. In aspects, the cancer is therapy-refractory.

In aspects, the ovarian cancer is recurrent or persistent epithelial ovarian, fallopian tube or primary peritoneal carcinoma. In aspects, the subjects received a platinum-taxane based chemotherapy regimen as their frontline therapy for ovarian cancer.

In some aspects, the colorectal cancer is histologically confirmed. In certain aspects, the colorectal cancer is metastatic or recurrent. In aspects, the subject has had progression during, after, or been intolerant following the last administration of standard therapies. In certain aspects, the subject has microsatellite instability. In other aspects, the colorectal cancer has low microsatellite instability (MSI-L).

In certain aspects, the melanoma is advance disease (previously treated, therapy-refractory or recurrent Stage III (unresectable) or Stage IV). In certain aspects, the patient with melanoma has a known BRAF V600 mutation. In certain aspects, the patient has melanoma that is no longer controlled by surgery, chemotherapy or radiotherapy. In aspects, the patient has melanoma that is refractory to or relapsed after surgery. In other aspects, the patient is treatment-naïve.

The present disclosure is further directed to determining a tumor mutational burden (TMB) status in a tumor of the subject. The disclosure is based on the fact that different tumor types exhibit different levels of immunogenicity and that tumor immunogenicity is directly related to TMB and/or neoantigen load.

As a tumor grows, it accumulates somatic mutations not present in germline DNA. Tumor mutation burden (TMB) refers to the number of somatic mutations in a tumor's genome and/or the number of somatic mutations per area of the tumor genome (after taking into account germline variant DNA). The acquisition of somatic mutations and, thus, a higher TMB can be influenced by distinct mechanisms, such as exogenous mutagen exposure (e.g., tobacco smoking or UV light exposure) and DNA mismatch repair mutations (e.g., MSI in colorectal and esophageal cancers). In solid tumors, about 95% of mutations are single-base substitutions. (Vogelstein et al., Science (2013) 339:1546-1558.) A "nonsynonymous mutation" herein refers to a nucleotide mutation that alters the amino acid sequence of a protein. Missense mutations and nonsense mutations can be both nonsynonymous mutations. A "missense mutation" herein refers to a nonsynonymous point mutation in which a single nucleotide change results in a codon that codes for a different amino acid. A "nonsense mutation" herein refers to a nonsynonymous point mutation in which a codon is changed to a premature stop codon that leads to truncation of the resulting protein.

In some embodiments, somatic mutations can be expressed at the RNA and/or protein level, resulting in neoantigens (also referred to as neoepitopes). Neoantigens can influence an immune-mediated anti-tumor response. For example, neoantigen recognition can promote T-cell activation, clonal expansion, and differentiation into effector and memory T-cells.

As a tumor develops, early clonal mutations (or "trunk mutations") can be carried by most or all tumor cells, while late mutations (or "branch mutations") can occur in only a subset of tumor cells or regions. (Yap et al., Sci Tranl Med (2012) 4:1-5; Jamai-Hanjani et al., (2015) Clin Cancer Res 21:1258-1266.) As a result, neoantigens derived from clonal "trunk" mutations are more widespread in the tumor genome than "branch" mutations and, thus, can lead to a high number of T cells reactive against the clonal neoantigen. (McGranahan et al., (2016) 351:1463-1469.) Generally, tumors with a high TMB can also have a high neoantigen load, which can lead to high tumor immunogenicity and increased T-cell reactivity and anti-tumor response. As such, cancers with a high TMB can respond well to treatment with immunotherapies, e.g., an anti-PD-1 antibody or anti-PD-L1 antibody.

Advances in sequencing technologies allow for evaluation of the tumor's genomic mutation landscape. Any sequencing methods known to those of skill in the art can be used to sequence nucleic acids from the tumor genome (e.g., obtained from a biological sample from a subject afflicted with a tumor). In one embodiment, PCR or qPCR methods, Sanger sequencing methods, or next-generation sequencing ("NGS") methods (such as genomic profiling, exome sequencing, or genome sequencing) can be used to measure TMB. In some embodiments, the TMB status is measured using genomic profiling. Genomic profiling involves analyzing nucleic acids from tumor samples, including coding and non-coding regions, and can be performed using methods having integrated optimized nucleic acid selection, read alignment, and mutation calling. In some embodiments, gene profiling provides next generation sequencing (NGS)-based analysis of tumors that can be optimized on a cancer-by-cancer, gene-by-gene, and/or site-by-site basis. Genome profiling can integrate the use of multiple, individually tuned, alignment methods or algorithms to optimize performance in sequencing methods, particularly in methods that rely on massively parallel sequencing of a large number of diverse genetic events in a large number of diverse genes. Genomic profiling provides for a comprehensive analysis of a subject's cancer genome, with clinical grade quality, and the output of the genetic analysis can be contextualized with relevant scientific and medical knowledge to increase the quality and efficiency of cancer therapy.

Genomic profiling involves a panel of a predefined set of genes comprising as few as five genes or as many as 1000 genes, about 25 genes to about 750 genes, about 100 genes to about 800 genes, about 150 genes to about 500 genes, about 200 genes to about 400 genes, about 250 genes to about 350 genes. In one embodiment, the genomic profile comprises at least 300 genes, at least 305 genes, at least 310 genes, at least 315 genes, at least 320 genes, at least 325 genes, at least 330 genes, at least 335 genes, at least 340 genes, at least 345 genes, at least 350 genes, at least 355 genes, at least 360 genes, at least 365 genes, at least 370 genes, at least 375 genes, at least 380 genes, at least 385 genes, at least 390 genes, at least 395 genes, or at least 400 genes. In another embodiment, the genomic profile comprises at least 325 genes. In a particular embodiment, the genomic profile comprises at least 315 cancer-related genes and introns in 28 genes (FOUNDATIONONE®) or the complete DNA coding sequence of 406 genes, introns in 31 genes with rearrangements, and the RNA sequence (cDNA) of 265 genes (FOUNDATIONONE® Heme). In another embodiment, the genomic profile comprises 26 genes and 1000 associated mutations (EXODX® Solid Tumor). In yet another embodiment, the genomic profile comprises 76 genes (Guardant360). In yet another embodiment, the genomic profile comprises 73 genes (Guardant360). In another embodiment, the genomic profile comprises 354 genes and introns in 28 genes for rearrangements (FOUNDATIONONE® CDX'). In certain embodiments, the genomic profile is FOUNDATIONONE® F1CDx. In another embodiment, the genomic profile comprises 468 genes (MSK-IMPACT™). One or more genes can be added to the genome profile as more genes are identified to be related to oncology.

The FOUNDATIONONE® assay is comprehensive genomic profiling assay for solid tumors, including but not limited to solid tumors of the lung, colon, and breast, melanoma, and ovarian cancer. The FOUNDATIONONE® assay uses a hybrid-capture, next-generation sequencing test to identify genomic alterations (base substitutions, insertions and deletions, copy number alterations, and rearrangements) and select genomic signatures (e.g., TMB and microsatellite instability). The assay covers 322 unique genes, including the entire coding region of 315 cancer-related genes, and selected introns from 28 genes. The full list of FOUNDATIONONE® assay genes is provided in Tables 2 and 3. See FOUNDATIONONE: Technical Specifications, Foundation Medicine, Inc., available at FoundationMedicine.com, last visited Mar. 16, 2018, which is incorporated by reference herein in its entirety.

In some embodiments, the subject who is treatable with the present methods (e.g., immunotherapy, e.g., a checkpoint inhibitor therapy) has a tumor mutational burden (TMB) that is high (≥10 mutations/megabase). In some embodiments, the assay measuring the TMB is a FOUNDATIONONE assay. In other embodiments, the subject who is treatable with the present methods have (i) a higher ratio of circulating TCM cells to circulating Teff cells ("TCM:Teff") relative to that in a human subject who has a tumor that does not have an inflammatory milieu; and (ii) a high TMB (≥10 mutations/megabase). In some embodiments, the subject who is treatable with the present methods have (i) a ratio of circulating TCM cells to circulating Teff cells ("TCM:Teff") that is similar to or higher than that in the top 90% (i.e., any values except the lower 10%) of healthy subjects and (ii) a high TMB (≥10 mutations/megabase).

In some embodiments, the present disclosure includes a method of treating a subject having cancer, comprising (i) determining the level of circulating TCM cells and the level of circulating Teff cells in a subject having cancer, and if the subject has a higher ratio of circulating TCM cells to circulating Teff cells ("TCM:Teff") relative to that in a human subject who has a tumor that does not have an inflammatory milieu, (ii) determining the TMB, and if the TMB is high, and then (iii) administering to the subject a checkpoint inhibitor. In some embodiments, the present disclosure is directed to a method of treating a subject having cancer, comprising (i) determining the level of circulating TCM cells and the level of circulating Teff cells in the subject, and if the subject has a ratio of circulating TCM cells to circulating Teff cells ("TCM:Teff") that is similar to or higher than that in the top 90% (i.e., any values except the lower 10%) of healthy subjects, (ii) determining the TMB, and if the TMB is high, and then (iii) administering to the subject a checkpoint inhibitor.

In some embodiments, the present disclosure includes a method of treating a subject having cancer, comprising (i) determining the level of circulating TCM cells and the level of circulating Teff cells in a subject having cancer, and if the subject has a higher ratio of circulating TCM cells to circulating Teff cells ("TCM:Teff") relative to that in a human subject who has a tumor that does not have an inflammatory milieu, (ii) determining the TMB and/or the level of PD-L1 in a tumor, and if the TMB is high and/or if PD-L1 level is ≥1% or ≥5%, and then administering to the subject a checkpoint inhibitor. In some embodiments, the present disclosure is directed to a method of treating a subject having cancer, comprising (i) determining the level of circulating TCM cells and the level of circulating Teff cells in the subject, and if the subject has a ratio of circulating TCM cells to circulating Teff cells ("TCM:Teff") that is similar to or higher than that in the top 90% (i.e., any values except the lower 10%) of healthy subjects, (ii) determining the TMB and/or the level of PD-L1 in a tumor of the subject, and if the TMB is high and/or if PD-L1 level is ≥1% or ≥5%, and then (iii) administering to the subject a checkpoint inhibitor.

In the methods described herein, administration of a checkpoint inhibitor may be substituted with a checkpoint stimulator, e.g., an agonist of a protein that stimulates the immune system, e.g., GITR, OX40, CD147, ICOS, CD27, HVEM, NKG2D or their binding partner.

Anti-PD-1 Antibodies or Anti-PD-L1 Antibodies Useful for the Invention

Certain aspects of the present disclosure comprise administering to a subject in need thereof a therapeutically effective amount of an anti-PD-1 antibody or an antigen binding portion thereof. HuMAbs that bind specifically to PD-1 with high affinity have been disclosed in U.S. Pat. No. 8,008,449. Other anti-PD-1 mAbs have been described in, for example, U.S. Pat. Nos. 6,808,710, 7,488,802, 8,168,757 and 8,354,509, and PCT Publication No. WO 2012/145493. Each of the anti-PD-1 HuMAbs disclosed in U.S. Pat. No. 8,008,449 has been demonstrated to exhibit one or more of the following characteristics: (a) binds to human PD-1 with a $K_D$ of $1\times10^{-7}$M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h)

stimulates antigen-specific memory responses; (i) stimulates antibody responses; and (j) inhibits tumor cell growth in vivo. Anti-PD-1 Abs usable in the present invention include mAbs that bind specifically to human PD-1 and exhibit at least one, in some aspects, at least five, of the preceding characteristics. In some aspects, the anti-PD-1 antibody is nivolumab. In one aspect, the anti-PD-1 antibody is pembrolizumab.

In one aspect, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9): 846-56).

In another aspect, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also www.cancer.gov/drugdictionary?cdrid=695789 (last accessed: Dec. 14, 2014). Pembrolizumab has been approved by the FDA for the treatment of relapsed or refractory melanoma.

In other aspects, the anti-PD-1 antibody cross-competes with MEDI0608. In still other aspects, the anti-PD-1 antibody binds to the same epitope as MEDI0608. In certain aspects, the anti-PD-1 antibody has the same CDRs as MEDI0608. In other aspects, the anti-PD-1 antibody is MEDI0608 (formerly AMP-514), which is a monoclonal antibody. MEDI0608 is described, for example, in U.S. Pat. No. 8,609,089B2.

In certain aspects, an immune checkpoint inhibitor is AMP-224, which is a B7-DC Fc fusion protein. AMP-224 is discussed in U.S. Publ. No. 2013/0017199 or in www.cancer.gov/publications/dictionaries/cancer-drug?cdrid=700595 (last accessed Jul. 8, 2015).

In certain aspects, the anti-PD-1 antibody is BGB-A317, which is a humanized monoclonal antibody. BGB-A317 is described in U.S. Publ. No. 2015/0079109.

In certain embodiments the anti-PD-1 antibody is PDR-001 (Novartis).

Anti-PD-1 antibodies usable in the disclosed methods also include isolated Abs that bind specifically to human PD-1 and cross-compete for binding to human PD-1 with nivolumab (see, e.g., U.S. Pat. Nos. 8,008,449 and 8,779,105; WO 2013/173223). The ability of Abs to cross-compete for binding to an antigen indicates that these Abs bind to the same epitope region of the antigen and sterically hinder the binding of other cross-competing Abs to that particular epitope region. These cross-competing Abs are expected to have functional properties very similar those of nivolumab by virtue of their binding to the same epitope region of PD-1. Cross-competing Abs can be readily identified based on their ability to cross-compete with nivolumab in standard PD-1 binding assays such as Biacore analysis, ELISA assays or flow cytometry (see, e.g., WO 2013/173223).

In certain aspects, the antibodies that cross-compete for binding to human PD-1 with, or bind to the same epitope region of human PD-1 antibody, nivolumab are monoclonal antibodies. For administration to human subjects, these cross-competing antibodies are chimeric antibodies, or humanized or human Abs. Such chimeric, humanized or human monoclonal antibodies can be prepared and isolated by methods well known in the art.

Anti-PD-1 Abs usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_m$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

Anti-PD-1 antibodies suitable for use in the disclosed methods or compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain aspects, the anti-PD-1 antibody or antigen-binding portion thereof cross-competes with nivolumab for binding to human PD-1. In other aspects, the anti-PD-1 antibody or antigen-binding portion thereof is a chimeric, humanized or human monoclonal antibody or a portion thereof. In certain aspects, the antibody is a humanized antibody. In other aspects, the antibody is a human antibody. Abs of an IgG1, IgG2, IgG3 or IgG4 isotype can be used.

In certain aspects, the anti-PD-1 antibody or antigen-binding portion thereof comprises a heavy chain constant region that is of a human IgG1 or IgG4 isotype. In certain other aspects, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014 *Cancer Immunol Res.* 2(9):846-56). In yet other aspects, the antibody comprises a light chain constant region that is a human kappa or lambda constant region. In other aspects, the anti-PD-1 antibody or antigen-binding portion thereof is a mAb or an antigen-binding portion thereof. In certain aspects of any of the therapeutic methods described herein comprising administration of an anti-PD-1 antibody, the anti-PD-1 antibody is nivolumab. In other aspects, the anti-PD-1 antibody is pembrolizumab. In other aspects, the anti-PD-1 antibody is chosen from the human antibodies 17D8, 2D3, 4H1, 4A11, 7D3 and 5F4 described in U.S. Pat. No. 8,008,449. In still other aspects, the anti-PD-1 antibody is MEDI0608 (formerly AMP-514), AMP-224, or BGB-A317.

In certain aspects, an anti-PD-1 antibody used in the methods can be replaced with another PD-1 or anti-PD-L1 antagonist. For example, because an anti-PD-L1 antibody prevents interaction between PD-1 and PD-L1, thereby exerting similar effects to the signaling pathway of PD-1, an anti-PD-L1 antibody can replace the use of an anti-PD-1 antibody in the methods disclosed herein. Therefore, certain aspects of the present disclosure comprise administering to a subject in need thereof a therapeutically effective amount of an anti-PD-L1 antibody or an antigen binding portion thereof. In certain aspects, the anti-PD-L1 antibody useful for the method is BMS-936559 (formerly 12A4 or MDX-1105) (see, e.g., U.S. Pat. No. 7,943,743; WO 2013/173223). In other aspects, the anti-PD-L1 antibody is MPDL3280A (also known as atezolizumab (TECENTRIQ) and RG7446) (see, e.g., Herbst et al. (2013) *J Clin Oncol* 31(suppl):3000. Abstract; U.S. Pat. No. 8,217,149), MEDI4736 (also called durvalumab (IMFINZI); Khleif (2013) In: Proceedings from the European Cancer Congress 2013; Sep. 27-Oct. 1, 2013; Amsterdam, The Netherlands) or avelumab (BAVENCIO; MSB0010718C). In some aspects, the anti-PD-L1 monoclonal antibody is selected from the group consisting of 28-8, 28-1, 28-12, 29-8, 5H1, and any combination thereof. In certain aspects, the antibodies that cross-compete for binding to human PD-L1 with, or bind to the same epitope region of human PD-L1 as the above-references PD-L1 antibodies are mAbs. In certain aspects, the anti-PD-L1 antibody or the antigen binding portion thereof competes for binding with BMS-936559, MPDL3280A, MEDI4736, or MSB0010718C for binding to human PD-L1. For administration to human subjects, these cross-competing antibodies can be chimeric antibodies, or can be humanized or human antibodies. Such chimeric, humanized or human mAbs can be prepared and isolated by methods well known in the art. See U.S. Pat. No. 8,779,108 or US 2014/0356353, filed May 6, 2014), or MSB0010718C (also called Avelumab; See US 2014/0341917). In certain aspects, the anti-PD-L1 antibody or antigen-binding portion thereof comprises a heavy chain constant region which is of a human IgG1 or IgG4 isotype. In some aspects, the anti-PD-L1 antibody is BMS-936559. In some aspects, the anti-PD-L1 antibody is MPDL3280A. In some aspects, the anti-PD-L1 antibody is MEDI4736. In some aspects, the anti-PD-L1 antibody is MSB0010718C.

Pharmaceutical Compositions and Dosages

Therapeutic agents of the present invention can be constituted in a composition, e.g., a pharmaceutical composition containing one or more Abs and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In one aspect, the carrier for a composition containing an antibody is suitable for intravenous, intramuscular, subcutaneous, parenteral, spinal or epidermal administration (e.g., by injection or infusion). A pharmaceutical composition of the invention can include one or more pharmaceutically acceptable salts, anti-oxidant, aqueous and non-aqueous carriers, and/or adjuvants such as preservatives, wetting agents, emulsifying agents and dispersing agents.

The present disclosure provides dosage regimens that can provide a desired response, e.g., a maximal therapeutic response and/or minimal adverse effects. For administration of an anti-PD-1 antibody (or an anti-PD-L1 antibody), the dosage can range from about 0.01 to about 10 mg/kg, about 1 to about 9 mg/kg, about 2 to about 8 mg/kg, about 3 to about 7 mg/kg, about 3 to about 6 mg/kg, 0.01 to about 5 mg/kg, or about 1 to about 3 mg/kg of the subject's body weight. For example, dosages can be about 0.1, about 0.3, about 1, about 2, about 3, about 4, about 5, about 6, about 7, about 8, about 9, or about 10 mg/kg body weight. The dosing schedule is typically designed to achieve exposures that result in sustained receptor occupancy (RO) based on typical pharmacokinetic properties of an antibody. An exemplary treatment regime entails administration once about every 1 week, once about every 2 weeks, once about every 3 weeks, once about every 4 weeks, once about every month, once about every 3-6 months or longer. In certain aspects, an anti-PD-1 antibody such as nivolumab is administered to the subject once about every 2 weeks. The anti-PD-1 antibody can be administered in at least two doses, each of the doses is at an amount of about 0.01 mg/kg to about 5 mg/kg, e.g., 3 mg/kg, at a dosing interval of every two weeks between the two doses. In some aspects, the anti-PD-1 (or an anti-PD-L1 antibody) antibody is administered in at least three, four, five, six, or seven doses (i.e., multiple doses), each of the doses is at an amount of about 0.01 mg/kg to about 10 mg/kg, e.g., 1 mg/kg, 3 mg/kg, or 6 mg/kg, at a dosing interval of every two weeks between two adjacently given doses. The dosage and scheduling can change during a course of treatment. In one aspect, a dosage regimen for an anti-PD-1 antibody (or an anti-PD-L1 antibody) of the present disclosure comprises about 0.1 to about 5 mg/kg body weight, about 1 to about 5 mg/kg body weight, or about 1 to about 3 mg/kg body weight via intravenous administration, with the antibody being given every about 14-21 days in up to about 6-week or about 12-week cycles until complete response or confirmed progressive disease. In some aspects, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years. In one aspect, the anti-PD-1 antibody or antigen-binding portion thereof or the anti-PD-L1 antibody or antigen-binding portion thereof is administered at a dose ranging from at least about 0.1 to at least about 10.0 mg/kg body weight once every about 2, about 3 or about 4 weeks. In one particular aspect, the anti-PD-1 antibody or antigen-binding portion thereof or the anti-PD-L1 antibody or antigen-binding portion thereof is administered at a dose of at least about 3 mg/kg body weight once about every 2 weeks.

When used in combinations with other therapies (e.g., other immunotherapies), the dosage of an anti-PD-1 antibody (or an anti-PD-L1 antibody) can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some aspects, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some aspects, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al. (2010) *J Clin Oncol* 28:3167-75). Thus, 0.3 mg/kg dosing can allow for sufficient exposure to lead to maximal biologic activity.

In some aspects of the invention, the anti-PD-1 antibody or the anti-PD-L1 antibody is administered at a dose of 3 mg/kg. In other aspects of the invention, the anti-PD-1 antibody or the anti-PD-L1 antibody is administered at a dose of 1 mg/kg.

In certain aspects, the dose of an anti-PD-1 antibody (or an anti-PD-L1 antibody) is a fixed dose in a pharmaceutical composition. In other aspects, the method of the present invention can be used with a flat dose (a dose given to a patient irrespective of the body weight of the patient). In aspects, the flat dose of the anti-PD-1 antibody or antigen binding portion thereof is at least about 100 mg, 120 mg, 140 mg, 160 mg, 180 mg, 200 mg, 220 mg, 240 mg, 260 mg, 280 mg, 300 mg, 400 mg, 420 mg, 440 mg, 460 mg, 480 mg, 500 mg, 520 mg, 540 mg, 560 mg or 600 mg. For example, a flat dose of a nivolumab can be about 240 mg. For example, a flat dose of pembrolizumab can be about 200 mg. In aspects, the anti-PD-1 antibody or antigen-binding portion thereof is administered at a dose of about 240 mg. In aspects, the anti-PD-1 antibody or antigen-binding portion thereof is administered at a dose of about 360 mg. In aspects, the anti-PD-1 antibody or antigen-binding portion thereof is administered at a dose of about 480 mg. In aspects, the flat dose of the anti-PD-1 antibody or antigen binding portion thereof is administered once about every week, every two weeks, every three weeks, every four weeks, every five weeks, or every six weeks. In one aspect, 360 mg of the anti-PD-1 antibody is administered once every 3 weeks. In another aspect, 480 mg of the anti-PD-1 antibody is administered once every 4 weeks.

Dosage and frequency vary depending on the half-life of the antibody in the subject. In general, human Abs show the longest half-life, followed by humanized Abs, chimeric Abs, and nonhuman Abs. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, or until the patient shows partial or complete amelioration of symptoms of disease. Thereafter, the patient can be administered a prophylactic regime.

Actual dosage levels of the active ingredients in the pharmaceutical compositions of the present invention can be varied so as to obtain an amount of the active ingredient that is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

EMBODIMENTS

Embodiment 1. A method of determining the existence of an inflammatory milieu in a tumor of a human subject having cancer, comprising determining the level of circulating central memory T ("TCM") cells and the level of circulating T effector memory ("Teff") cells in the subject, wherein a higher ratio of circulating TCM cells to circulating Teff cells ("TCM:Teff") in the subject relative to that in a human subject who has a tumor that does not have an inflammatory milieu indicates that the tumor milieu is inflamed.

Embodiment 2. A method of determining the existence of an inflammatory milieu in a tumor of a human subject having cancer, comprising determining the level of circulating TCM cells and the level of circulating Teff cells in the subject, wherein a ratio of circulating TCM cells to circulating Teff cells ("TCM:Teff") that is similar to or higher than that in the top 90% (i.e., any values except the lower 10%) of healthy subjects (or controls) indicates that the tumor milieu is inflamed.

Embodiment 3. A method of determining the likelihood of response of a human subject having cancer to a checkpoint inhibitor, comprising determining the level of circulating TCM cells and the level of circulating Teff cells in the subject, wherein a higher ratio of circulating TCM cells to circulating Teff cells ("TCM:Teff") in the subject relative to that in a human subject who has a tumor that does not have an inflammatory milieu indicates that the subject is likely to respond to a checkpoint inhibitor.

Embodiment 4. A method of determining the likelihood of response of a human subject having cancer to a checkpoint inhibitor, comprising determining the level of circulating TCM cells and the level of circulating Teff cells in the subject, wherein a ratio of circulating TCM cells to circulating Teff cells ("TCM:Teff") that is similar to or higher than that in the top 90% of healthy subjects indicates that the subject is likely to respond to a checkpoint inhibitor.

Embodiment 5. The method of any one of embodiments 1-4, wherein the TCM cells and the Teff cells are CD4+ TCM and CD4+ Teff cells, respectively.

Embodiment 6. The method of any one of embodiments 1-4, wherein the TCM cells and the Teff cells are CD8+ TCM and CD8+ Teff cells, respectively.

Embodiment 7. The method of embodiment 1, comprising determining the level of circulating CD4+ TCM cells, circulating CD8+ TCM, circulating CD4+ Teff cells, and circulating CD8+ Teff cells, wherein both (i) a higher ratio of circulating CD4+ TCM cells to circulating CD4 Teff ("CD4+ TMC:CD4+ Teff) cells and (ii) a higher ratio of circulating CD8+ TCM cells to circulating CD8 Teff ("CD8+ TMC:CD8+ Teff) cells relative to those, respectively, in a human subject who has a tumor that does not have an inflammatory milieu, indicates that the tumor milieu is inflamed.

Embodiment 8. The method of embodiment 2, comprising determining the level of circulating CD4+ TCM cells, circulating CD8+ TCM, circulating CD4+ Teff cells, and circulating CD8+ Teff cells, wherein both (i) a ratio of circulating CD4+ TCM cells to circulating CD4 Teff cells ("CD4+ TMC:CD4+ Teff") and (ii) a ratio of circulating CD8+ TCM cells to circulating CD8 Teff cells ("CD8+ TMC:CD8+ Teff") that is similar to or higher than that, respectively, in the top 90% of healthy subjects indicates that the tumor milieu is inflamed.

Embodiment 9. The method of embodiment 3, comprising determining the level of circulating CD4+ TCM cells, circulating CD8+ TCM, circulating CD4+ Teff cells, and circulating CD8+ Teff cells, wherein both (i) a higher ratio of circulating CD4+ TCM cells to circulating CD4 Teff ("CD4+ TMC:CD4+ Teff") cells and (ii) a higher ratio of circulating CD8+ TCM cells to circulating CD8 Teff ("CD8+ TMC:CD8+ Teff") cells relative to those, respectively, in a human subject who has a tumor that does not have an inflammatory milieu, indicates that the subject is likely to respond to a checkpoint inhibitor.

Embodiment 10. The method of embodiment 4, comprising determining the level of circulating CD4+ TCM cells, circulating CD8+ TCM, circulating CD4+ Teff cells, and circulating CD8+ Teff cells, wherein both (i) a ratio of circulating CD4+ TCM cells to circulating CD4 Teff ("CD4+ TMC:CD4+ Teff) cells and (ii) a ratio of circulating CD8+ TCM cells to circulating CD8 Teff ("CD8+ TMC:CD8+ Teff) cells that is similar to or higher than that, respectively, in the top 90% of healthy subjects indicates that the subject is likely to respond to a checkpoint inhibitor.

Embodiment 11. The method of any one of embodiments 1-10, wherein the TCM cells are CCR7+ and CD45RA−.

Embodiment 12. The method of any one of embodiments 1-10, wherein the Teff cells are CCR7− and CD45RA+.

Embodiment 13. The method of any one of embodiments 3, 4, 9 and 10, wherein the checkpoint inhibitor is a PD-1/PD-L1 axis antagonist.

Embodiment 14. The method of embodiment 13, wherein the checkpoint inhibitor is a PD-1 antagonist.

Embodiment 15. The method of embodiment 14, wherein the PD-1 antagonist is a PD-1 antibody.

Embodiment 16. The method of embodiment 15, wherein the PD-1 antibody is nivolumab.

Embodiment 17. The method of embodiment 15, wherein the PD-1 antibody is pembrolizumab, PDR001, REGN2810, AMP-514 (MEDI0608) or BGB-A317.

Embodiment 18. The method of embodiment 13, wherein the checkpoint inhibitor is a PD-L1 antagonist.

Embodiment 19. The method of embodiment 18, wherein the PD-L1 antagonist is a PD-L1 antibody.

Embodiment 20. The method of embodiment 19, wherein the PD-L1 antibody is atezolizumab, durvalumab or avelumab.

Embodiment 21. The method of any one of embodiments 3, 4, 9 and 10, wherein the checkpoint inhibitor is an antagonist of CTLA-4, LAG-3, TIM3, CEACAM-1, BTLA, CD69, TIGIT, CD113, GPR56, VISTA, 2B4, CD48, GARP, CD73, PD1H, LAIR1, TIM-1,TIM-4, CD39, CSF-1R or IDO.

Embodiment 22. A method of treating a subject having cancer, comprising administering a checkpoint inhibitor to a subject having a higher ratio of circulating TCM cells to circulating Teff cells ("TCM:Teff") relative to that in a human subject who has a tumor that does not have an inflammatory milieu indicates that the tumor milieu is inflamed.

Embodiment 23. A method of treating a subject having cancer, comprising administering a checkpoint inhibitor to a subject having a ratio of circulating TCM cells to circulating Teff cells ("TCM:Teff") that is similar to or higher than that in the top 90% (i.e., any values except the lower 10%) of healthy subjects.

Embodiment 24. A method of treating a subject having cancer, comprising
  determining the level of circulating TCM cells and the level of circulating Teff cells in a subject having cancer, and if the subject has a higher ratio of circulating TCM cells to circulating Teff cells ("TCM:Teff") relative to that in a human subject who has a tumor that does not have an inflammatory milieu,
  administering to the subject a checkpoint inhibitor.

Embodiment 25. A method of treating a subject having cancer, comprising
  determining the level of circulating TCM cells and the level of circulating Teff cells in the subject, and if the subject has a ratio of circulating TCM cells to circulating Teff cells ("TCM:Teff") that is similar to or higher than that in the top 90% (i.e., any values except the lower 10%) of healthy subjects,
  administering to the subject a checkpoint inhibitor.

Embodiment 26. The method of any one of embodiments 22-25, wherein the TCM cells and the Teff cells are CD4+ TCM and CD4+ Teff cells, respectively.

Embodiment 27. The method of any one of embodiments 22-25, wherein the TCM cells and the Teff cells are CD8+ TCM and CD8+ Teff cells, respectively.

Embodiment 28. A method of treating a subject having cancer, comprising administering a checkpoint inhibitor to a subject having both (i) a higher ratio of circulating CD4+ TCM cells to circulating CD4 Teff ("CD4+ TMC:CD4+ Teff") cells and (ii) a higher ratio of circulating CD8+ TCM cells to circulating CD8 Teff ("CD8+ TMC:CD8+ Teff") cells relative to those, respectively, in a human subject who has a tumor that does not have an inflammatory milieu.

Embodiment 29. A method of treating a subject having cancer, comprising administering a checkpoint inhibitor to a subject having both (i) a ratio of circulating CD4+ TCM cells to circulating CD4 Teff ("CD4+ TMC:CD4+ Teff") cells and (ii) a ratio of circulating CD8+ TCM cells to circulating CD8 Teff ("CD8+ TMC:CD8+ Teff") cells that are similar to or higher than those, respectively, in the top 90% of healthy subjects.

Embodiment 30. A method of treating a subject having cancer, comprising
  determining the level of circulating CD4+ TCM cells, circulating CD8+ TCM, circulating CD4+ Teff cells, and circulating CD8+ Teff cells in a subject having cancer, and if the subject has both (i) a higher ratio of circulating CD4+ TCM cells to circulating CD4 Teff ("CD4+ TMC:CD4+ Teff") cells and (ii) a higher ratio of circulating CD8+ TCM cells to circulating CD8 Teff ("CD8+ TMC:CD8+ Teff") cells relative to those, respectively, in a human subject who has a tumor that does not have an inflammatory milieu,
  administering to the subject a checkpoint inhibitor.

Embodiment 31. A method of treating a subject having cancer, comprising
  determining the level of circulating CD4+ TCM cells, circulating CD8+ TCM, circulating CD4+ Teff cells, and circulating CD8+ Teff cells in a subject having cancer, and if the subject has both (i) a ratio of circulating CD4+ TCM cells to circulating CD4 Teff ("CD4+ TMC:CD4+ Teff") cells and (ii) a ratio of circulating CD8+ TCM cells to circulating CD8 Teff ("CD8+ TMC:CD8+ Teff") cells that are similar to or higher than those, respectively, in the top 90% of healthy subjects,
  administering to the subject a checkpoint inhibitor.

Embodiment 32. The method of any one of embodiments 22-31, wherein the TCM cells are CCR7+ and CD45RA−.

Embodiment 33. The method of any one of embodiments 22-32, wherein the Teff cells are CCR7− and CD45RA+.

Embodiment 34. The method of any one of embodiments 22-33, wherein the checkpoint inhibitor is a PD-1/PD-L1 axis antagonist.

Embodiment 35. The method of embodiment 34, wherein the checkpoint inhibitor is a PD-1 antagonist.

Embodiment 36. The method of embodiment 35, wherein the PD-1 antagonist is a PD-1 antibody.

Embodiment 37. The method of embodiment 36, wherein the PD-1 antibody is nivolumab.

Embodiment 38. The method of embodiment 36, wherein the PD-1 antibody is pembrolizumab, PDR001, REGN2810, AMP-514 (MEDI0608) or BGB-A317.

Embodiment 39. The method of embodiment 34, wherein the checkpoint inhibitor is a PD-L1 antagonist.

Embodiment 40. The method of embodiment 39, wherein the PD-L1 antagonist is a PD-L1 antibody.

Embodiment 41. The method of embodiment 40, wherein the PD-L1 antibody is atezolizumab, durvalumab or avelumab.

Embodiment 42. The method of any one of embodiments 22-41, wherein the checkpoint inhibitor is an antagonist of CTLA-4, LAG-3, TIM3, CEACAM-1, BTLA, CD69, TIGIT, CD113, GPR56, VISTA, 2B4, CD48, GARP, CD73, PD1H, LAIR1, TIM-1,TIM-4, CD39, CSF-1R or IDO.

Embodiment 43. The method of any one of embodiments 1-42, wherein the cancer or tumor is melanoma, lung cancer or kidney cancer.

Embodiment 44. The method of any one of embodiments 1-43, wherein the cancer is NSCLC.

Embodiment 45. The method of any one of embodiments 1-44, further comprising determining the tumor mutational burden (TMB) in a tumor of the subject.

Embodiment 46. The method of embodiment 45, wherein, if the tumor mutational burden (TMB) is high (≥10 mutations/megabase), an immunotherapy, such as a checkpoint inhibitor, is administered to the subject.

Embodiment 47. A method of treating a subject having cancer, comprising administering a checkpoint inhibitor to a subject having (i) a higher ratio of circulating TCM cells to circulating Teff cells ("TCM:Teff") relative to that in a human subject who has a tumor that does not have an inflammatory milieu; and (ii) a high TMB.

Embodiment 48. A method of treating a subject having cancer, comprising administering a checkpoint inhibitor to a subject having (i) a ratio of circulating TCM cells to circulating Teff cells ("TCM:Teff") that is similar to or higher than that in the top 90% (i.e., any values except the lower 10%) of healthy subjects and (ii) a high TMB.

Embodiment 49. A method of treating a subject having cancer, comprising
 determining the level of circulating TCM cells and the level of circulating Teff cells in a subject having cancer, and if the subject has a higher ratio of circulating TCM cells to circulating Teff cells ("TCM:Teff") relative to that in a human subject who has a tumor that does not have an inflammatory milieu, and
 determining the TMB, and if the TMB is high, then administering to the subject a checkpoint inhibitor.

Embodiment 50. A method of treating a subject having cancer, comprising
 determining the level of circulating TCM cells and the level of circulating Teff cells in the subject, and if the subject has a ratio of circulating TCM cells to circulating Teff cells ("TCM:Teff") that is similar to or higher than that in the top 90% (i.e., any values except the lower 10%) of healthy subjects, and
 determining the TMB, and if the TMB is high, then administering to the subject a checkpoint inhibitor.

Embodiment 51. The method of any one of embodiments 1-50, further comprising determining the level of PD-L1 in a tumor of the subject.

Embodiment 52. The method of embodiment 51, wherein an immunotherapy, such as with a checkpoint inhibitor, is only administered to the subject if PD-L1 level is ≥1% or ≥5%.

The present invention is further illustrated by the following example that should not be construed as further limiting. The contents of all references cited throughout this application are expressly incorporated herein by reference.

EXAMPLES

Example 1

Expanded CD8 Percentages in Most Cancer Patients

The number of peripheral CD8+ T cells was measured in human patients having melanoma, colon cancer, non-squamous non small cell lung cancer (NSNSCLC) or squamous lung cancer.

Fresh frozen melanoma (n=42) and NSNSCLC (n=40) FFPE tumor biopsies and peripheral blood mononuclear cells (PBMC) were provided by the Moffitt Cancer Center (Table 1). None of these patients had received treatment with checkpoint inhibitors. For local immune responses, gene expression data in FFPE tissues was measured to calculate inflammatory signature scores in the tumors (S. Spranger, R. Bao, T. F. Gajewski, Melanoma-intrinsic beta-catenin signaling prevents anti-tumor immunity. *Nature* 523, 231-235 (2015)). For systemic responses, flow cytometry for T cell subpopulations in PBMC (Table 2) was used. Control PBMC (n=26) were obtained from a blood donation program.

TABLE 1

Patients characteristics and demographics

| Cohort | Subjects | Age (mean age, SD) | Sex (M, %) | Stage II | Stage III | Stage IV |
|---|---|---|---|---|---|---|
| Control | 27 | 54.9 (8.5) | 11 (40.7%) | | | |
| Melanoma | 42 | 63.72 (15) | 32 (76%) | 1 | 17 | 24 |
| NSNSCLC | 40 | 65.67 (11.8) | 14 (35%) | 16 | 12 | 12 |

TABLE 2

Flow cytometry panel

| Marker | Fluorochrome | Clone |
|---|---|---|
| CD127 | AlexaFluor 488 | A0195D5 |
| Viability dye | Near infrared | |
| CD8 | APC-R700 | RPA-T8 |
| CD28 | BV650 | CD28.2 |
| CCR7 | BV421 | GO43H7 |
| CD25 | PE-Cy7 | M-A251 |
| CD279 | PE | EH12 |
| CD45RA | BUV395 | HI100 |
| CD4 | BUV496 | SK3 |
| CD3 | BUV737 | SK7 |

As shown on FIG. 1, most of these cancer patients have a larger fraction of peripheral CD8 T cells relative to that in healthy subjects.

Example 2

Cancer Patients have Expanded Effector T Cells

The percentage of naïve, central memory, effector memory and effector T cells among CD4+ and CD8+ T cells, respectively, was measured in healthy subjects (controls), melanoma patients, colon cancer patients, NSNSC lung cancer patients and squamous lung cancer patients and plotted as percentage of the total CD4+ and CD8+ Tcells, respectively.

Figure 2A:
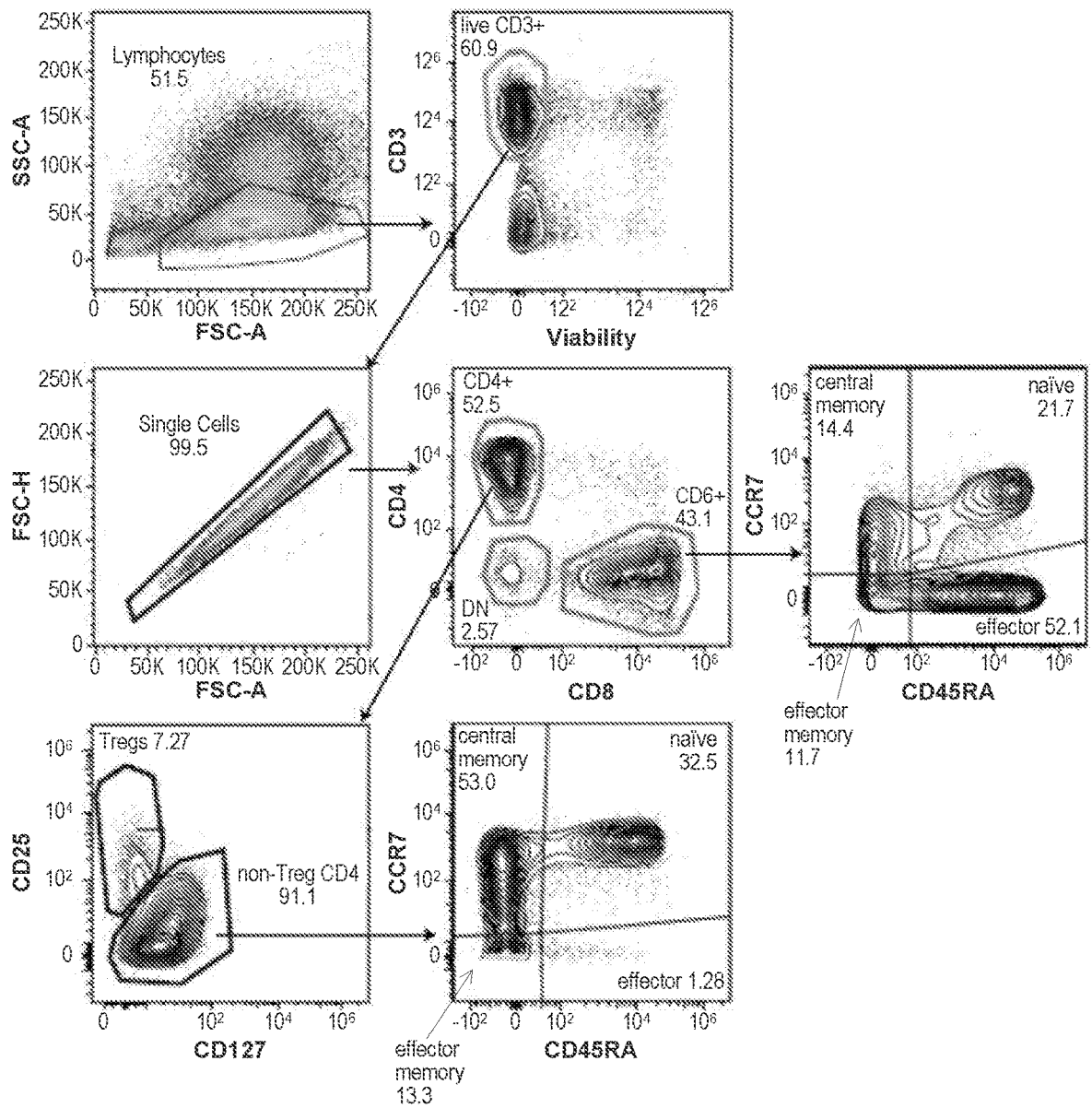
FIG. 2A shows the gating strategy to define CD4+ and CD8+ T cell subpopulations in peripheral cell mononuclear cells (PBMC). Populations of CD3+ cells, CD4+ Treg cells, non-Treg CD4+ cells, central memory CD4+ T cells, naïve CD4+ T cells, effector memory CD4+ T cells and effector CD4+ T cells, central memory CD8+ T cells, naïve CD8+ T cells, effector memory CD8+ T cells and effector CD8+ T cells are shown. FSC-H=forward scatter height; SSC-A=side scatter area CD4+ Tregs and CD4+ non-Treg cells are shown in the upper and lower cell population, respectively, of the top CD25/CD127 plot. Central memory, naïve, effector memory and effector T cells are shown in the top left quadrant, top right quadrant, lower left quadrant and lower right quadrant, respectively, of the CCR7/CD45RA plots.

The following surface markers were used to identify these cell types: CD3, CD4, CD8, CD45RA, and CCR7, as reported by Appay et at (V. Appay et al., Memory CD8+ T cells vary in differentiation phenotype in different persistent virus infections. Nature medicine 8, 379-385 (2002)). The flow cytometry antibody panel used is set forth in Example 1. Viable CD3+ singlets were separated into CD4+ and CD8+ subpopulations, and these subpopulations were later defined by their differentiation stage as naive, central memory, effector memory, and effector, based on their CD45RA and CCR7 expression. For CD4+ cells, regulatory T cells CD25hi and CD127negs were excluded before proceeding to gating by differentiation stage. The gating strategy used is shown in FIG. 2A.

Figure 2B:
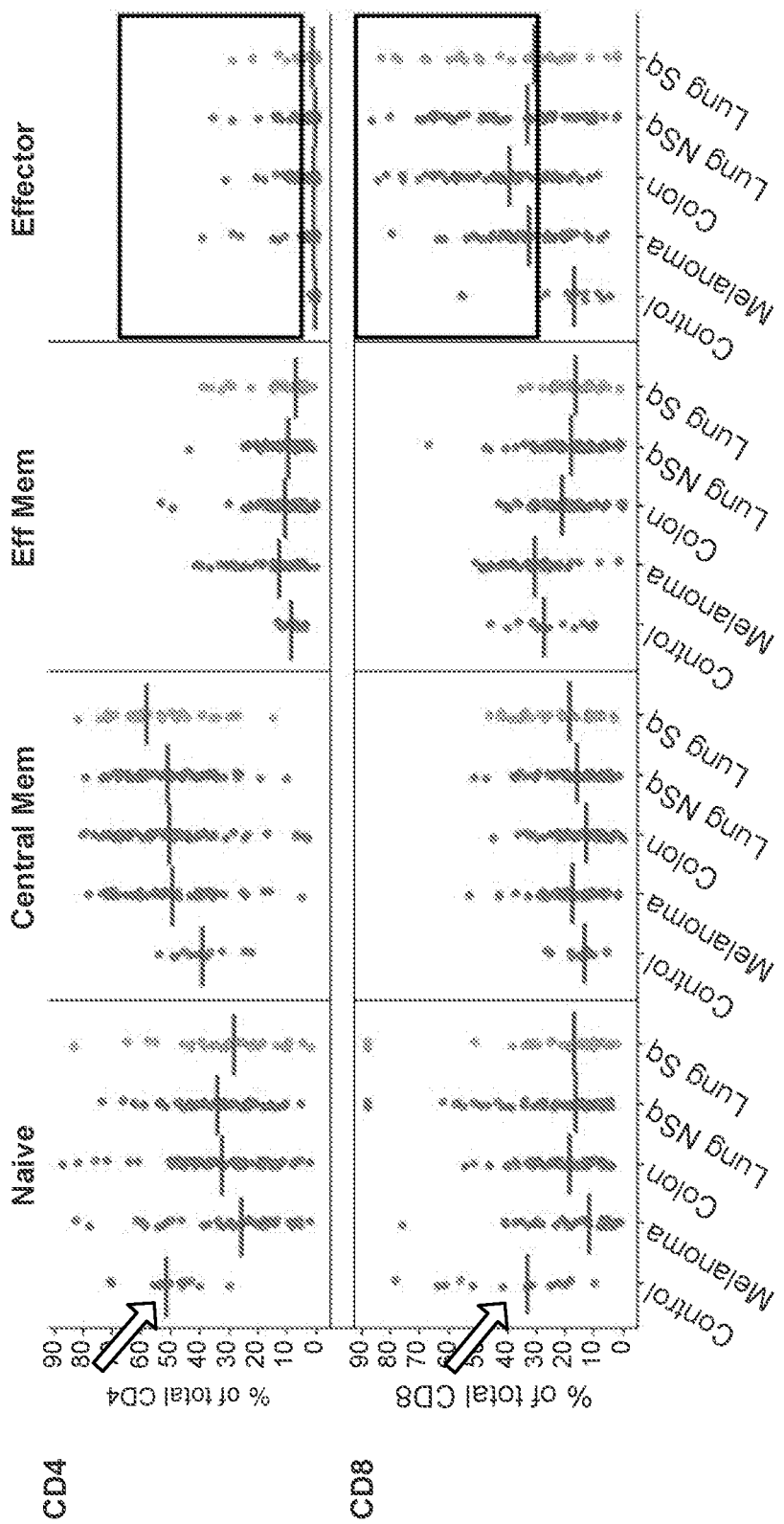
FIG. 2B shows the percentage of naïve T cells, central memory T ("TCM") cells, effector memory T ("TeffM") cells and effector T ("Teff") cells of total CD4+(top) and CD8+(bottom) T cells in healthy subjects ("control"), melanoma patients ("melanoma"), colon cancer patients ("colon"), non-squamous (NSNSCLC) lung cancer patients ("Lung Nsq") and squamous lung cancer patients ("Lung Sq"), showing that cancer patients have expanded effector T cell populations relative to healthy subjects.

The results, which are shown in FIG. 2B, indicate that cancer patients have expanded effector T cell populations and that there is evidence of an ongoing immune response in the peripheral blood of cancer patients.

Example 3

Circulating CD4+ Central Memory T Cells Increase with Inflammation Score in Melanoma The level of circulating CD4+ central memory T cells was measured in healthy subjects and in melanoma patients, and their levels were compared in patients at different stages of melanoma as well as in patients having different states of inflammation in their tumors.

The inflammation state of tumors was determined by scoring the inflammation gene signature, i.e., measuring the level of expression of 13 genes in FFPE tissues, whose level of expression were previously linked with the presence of a T cell infiltrate in tumors: CCL2, CCL3, CCL4, CD8A, CXCL10, CXCL9, CZMK, HLA-DMA, HLA-DMB, HLA-DOA, HLA-DOB, ICOS and IRF1 (Spranger, et al. Nature 523, 231-235 (2015)). Normalized RSEM values of each gene were padded by 0.1, log 2 transformed and mean centered across samples. The score was calculated as average of all genes after transformation.

Figures 3A, 3B:
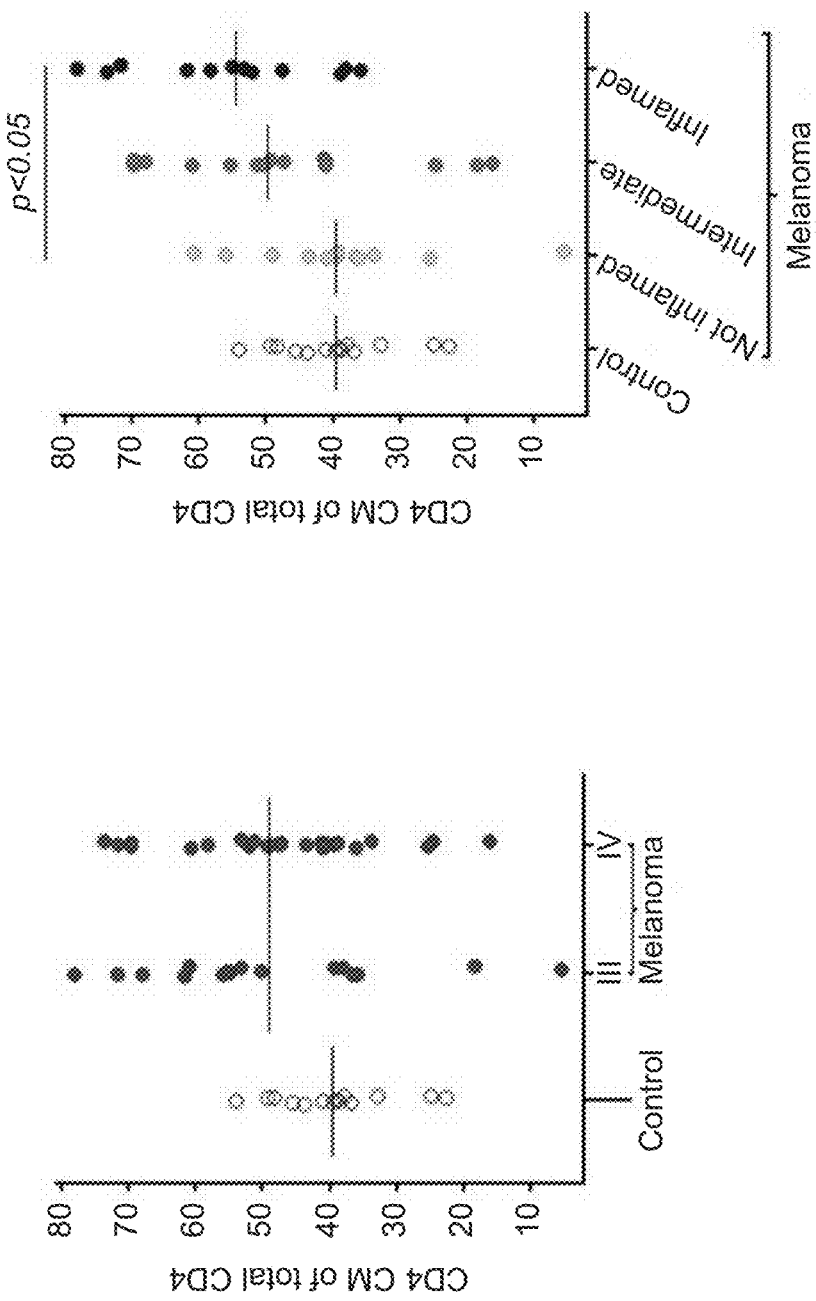
FIGS. 3A and 3B show the percentage of circulating CD4+ TCM cells in healthy subjects ("control"; first lane) or in melanoma patients (lanes 2 and 3 in FIG. 3A and lanes 2-4 in FIG. 3B) as a function of stage of the cancer (FIG. 3A) and as a function of the inflammation state of tumors (i.e., not inflamed, intermediate inflamed and inflamed.

The results, which are shown in FIGS. 3A-3B, indicate that the level of circulating CD4+ central memory T cells increases with inflammation score in melanoma. Thus, the level of CD4+ central memory T cells could be used as a biomarker of a pre-existing immune response to tumors, and a biomarker for clinical response to anti-PD1.

Example 4

Circulating Central Memory to Effector T Cell Ratios Correlate with Immune Inflammatory Signatures at the Tumor Site in Melanoma and Non-Squamous Non-Small Cell Lung Cancer The level of circulating CD4+ and CD8+ central memory and effector T cells and level of inflammation in the tumor milieu were measured in melanoma and non-squamous lung cancer patients.

Stage II through IV Melanoma (n=42) and non-squamous non-small cell lung (n=40) Archived Formalin-fixed, Paraffin-embedded (FFPE) tumor biopsies and peripheral blood mononuclear cells (PBMC) were used. None of these patients had received treatment with checkpoint inhibitors.

The level of CD4+ central memory T cells and the inflammation state was measured as described in the previous Examples. The level of CD8+ central memory T cells was determined as described for the CD4+ central memory T cells, but with a CD8+ marker instead of a CD4+ marker. The level of CD4+ effector T cells and CD8+ effector T cells ("TCM" or "CMT") were determined by measuring the number of CD4+CCR7− CD45RA+ T cells and CD8+ CCR7-CD45RA+ T cells, respectively, by flow cytometry.

Figure 4A:
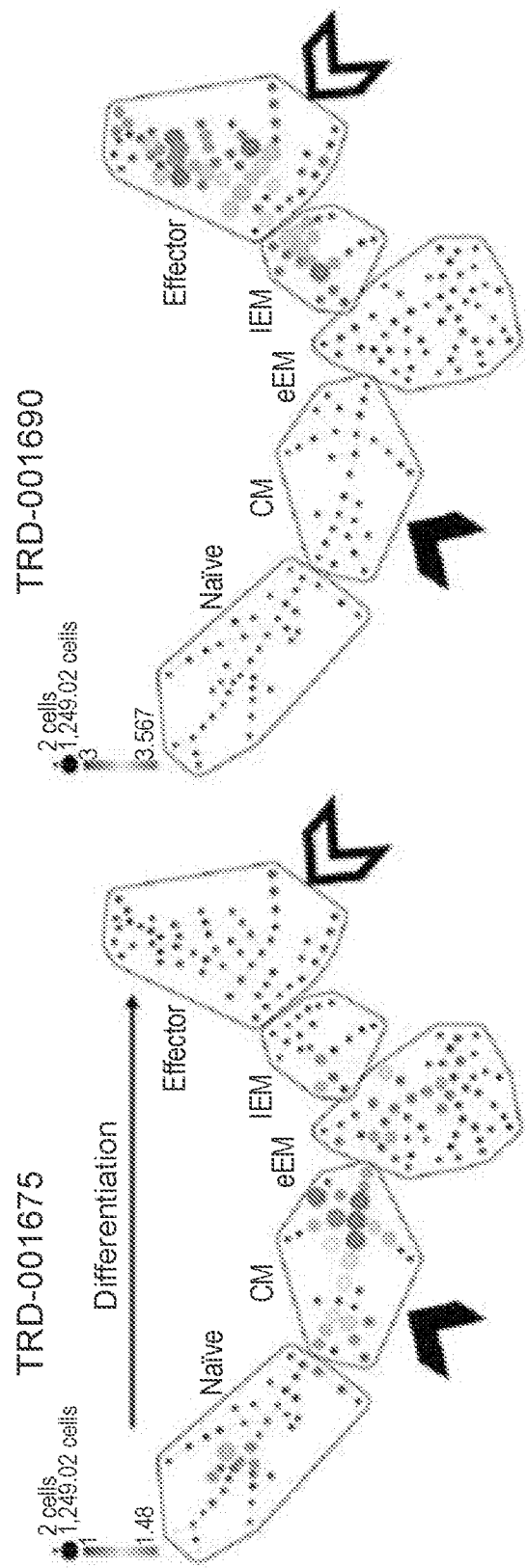
FIG. 4A shows the spanning-tree progression analysis of density-normalized events (SPADE)-generated maturation profiles of CD8+ T cells for two melanoma samples.

FIG. 4A shows SPADE-generated maturation profiles of CD8+ T cells for two melanoma samples.

FIG. 4B shows the inverse correlation between the level of CD4+ central memory and effector T cells, and that of CD8+ central memory and effector T cells in melanoma patients.

Figure 4C:
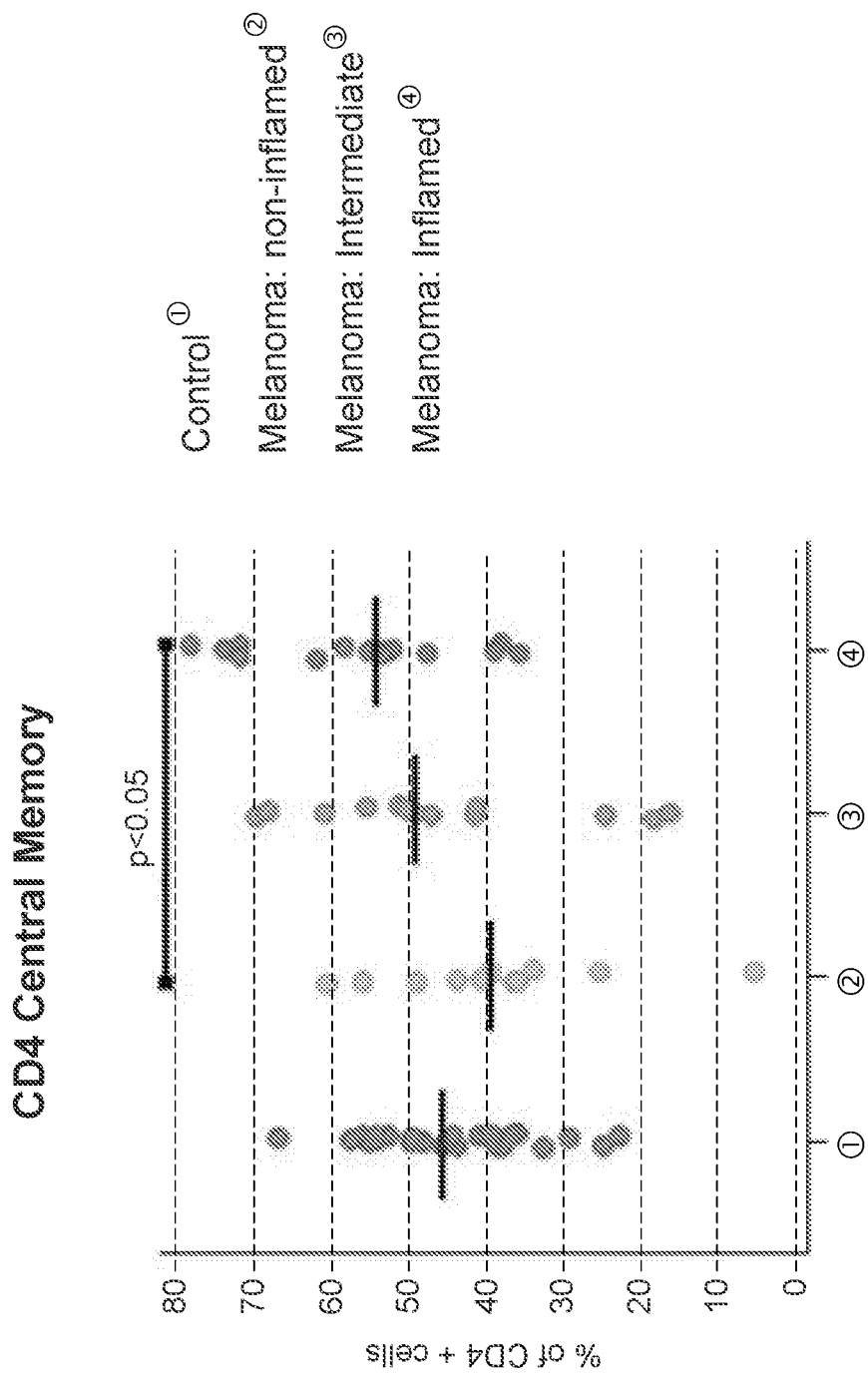
FIG. 4C shows the correlation between circulating CM CD4$^+$ cells and local immune responses quantified with the gene expression signature reported in S. Spranger, R. Bao, T. F. Gajewski, Melanoma-intrinsic beta-catenin signalling prevents anti-tumour immunity. *Nature* 523, 231-235 (2015). From left to right: control; melanoma non-inflamed; melanoma intermediate and melanoma inflamed.

The number of CD4+ central memory cells as a percentage of CD4+ T cells was measured in control, melanoma patients with non-inflamed tumors, melanoma patients with intermediate inflamed tumors and in melanoma patients with inflamed tumors. The results are shown in FIG. 4C.

Figure 4D:
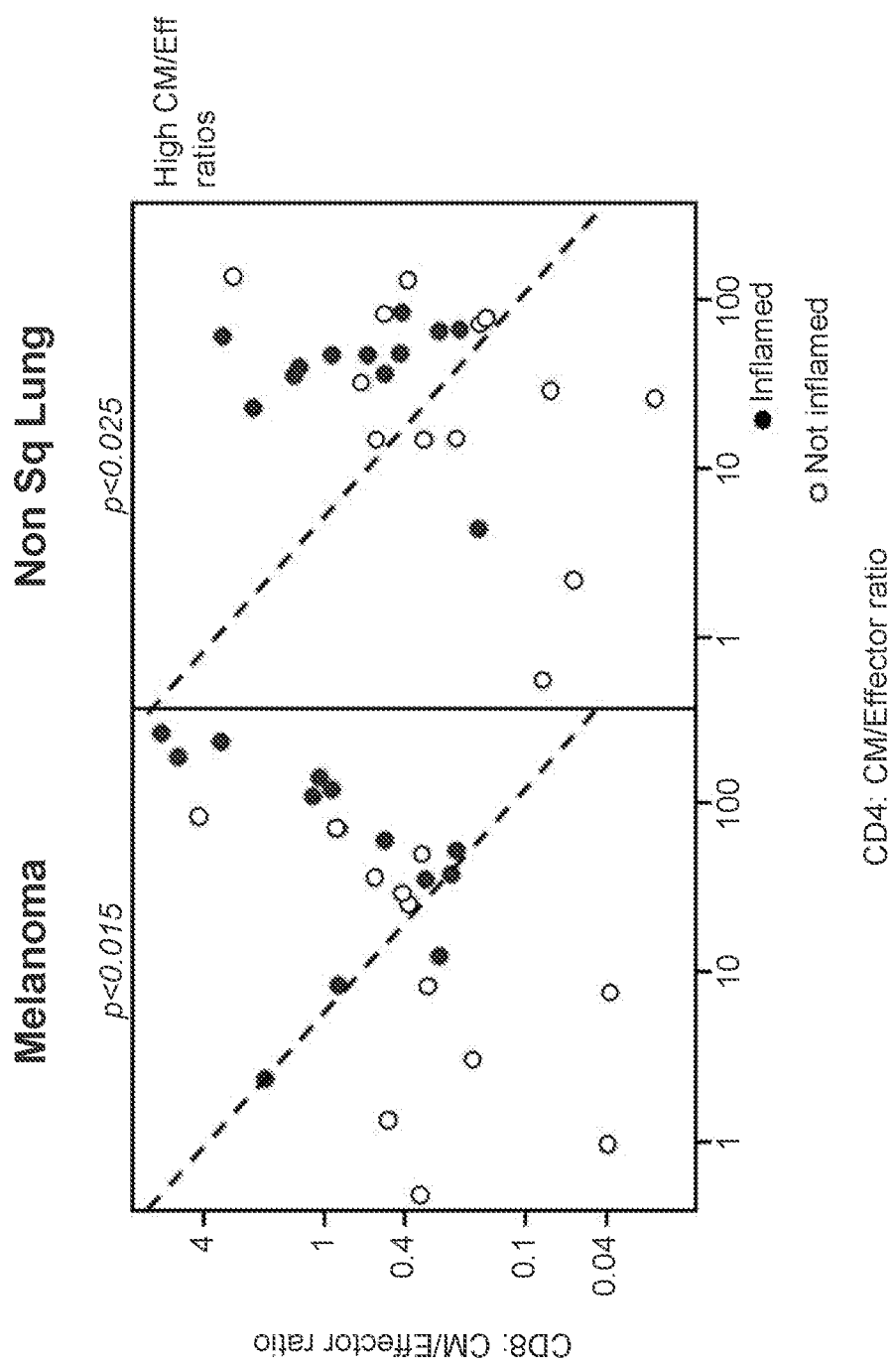
FIG. 4D shows the ratio of CD8+ central memory ("CM") T cells to effector T cells as a function of the ratio of CD4+ central memory ("CM") T cells to effector T cells in melanoma and non-squamous non-small cell lung cancer patients having either inflamed (close circles) or not inflamed (open circles) tumors (every spot corresponds to a given patient), indicating that the maturation profiles of CD4 and CD8 cells in blood correlate with the inflammatory signature at the tumor site.

The ratio of the number of central memory T cells to effector T cells was determined for CD4+ and CD8+ cells, and the ratios plotted on a graph with the x axis representing the ratio of CD4+ central memory T cells to CD4+ effector T cells and the y axis representing the ratio of CD8+ central memory T cells to CD4+ effector T cells. This was done for melanoma patients and non-squamous lung cancer patients. The graphs are shown in FIG. 4D, and each dot in the graphs represent one patient. When considering the inflammatory score of the tumors of the patients, it can be seen that patients with a high inflammatory score are mostly patients having a high ratio of CD4+ central memory to effector T cells and a high ratio to CD8+ central memory to effector T cells. Thus, patients with melanoma and non-squamous lung cancer who have an inflammatory milieu in the tumor as determined by inflammatory signature score have increased circulating central memory T cells (CCR7+, CD45RA−) and decreased effector T cells (CCR7-, CD45RA+), and when calculating central memory to effector (CM/Eff) ratios, it was observed that tumors defined as "inflamed" based on transcriptional signature scores, could be identified with high sensitivity (Melanoma: 92%, 95% CI: 66.13-99.8%; non-squamous non-small cell cancer (91%, 95% CI: 61.52-99.8%).

The results show that melanoma and lung cancer patients who have higher inflammation score in the tumor show increased circulating central memory and decreased effector cells both in CD4 and CD8 T cells. Thus, the ratio of circulating central memory to effector T cell frequencies in circulating CD4+ and/or CD8+ T cells could be used as a biomarker of intra-tumor inflammatory score, with the advantage that no tumor biopsy has to be obtained from the patient.

There are distinct circulating T cell maturation patterns that distinguish between control samples and those belonging to patients with the studied tumors. We detected particular circulating T cell profiles in patients with melanoma and non-squamous lung cancer who have an inflammatory milieu in the tumor as determined by inflammatory signature score.

These findings represent progress in the characterization of peripheral immunity, as it relates to the inflammatory immune status in the tumor. The results also provide potential approaches to measure the immune response to cancer in peripheral blood, which are more easily accessible relative to tumor biopsies.

Example 5

Higher CM/Eff Ratios in Patients Who Show Response to Anti-PD1 Agents

Samples of healthy subjects and cancer patients who have received treatment with an anti-PD-1 agent were analyzed for levels of circulating CD4+ and CD8+ naïve T cells, central memory T cells, effector memory T cells and effector T cells. The cancer patients had melanoma, lung cancer or kidney cancer.

Figure 5A:
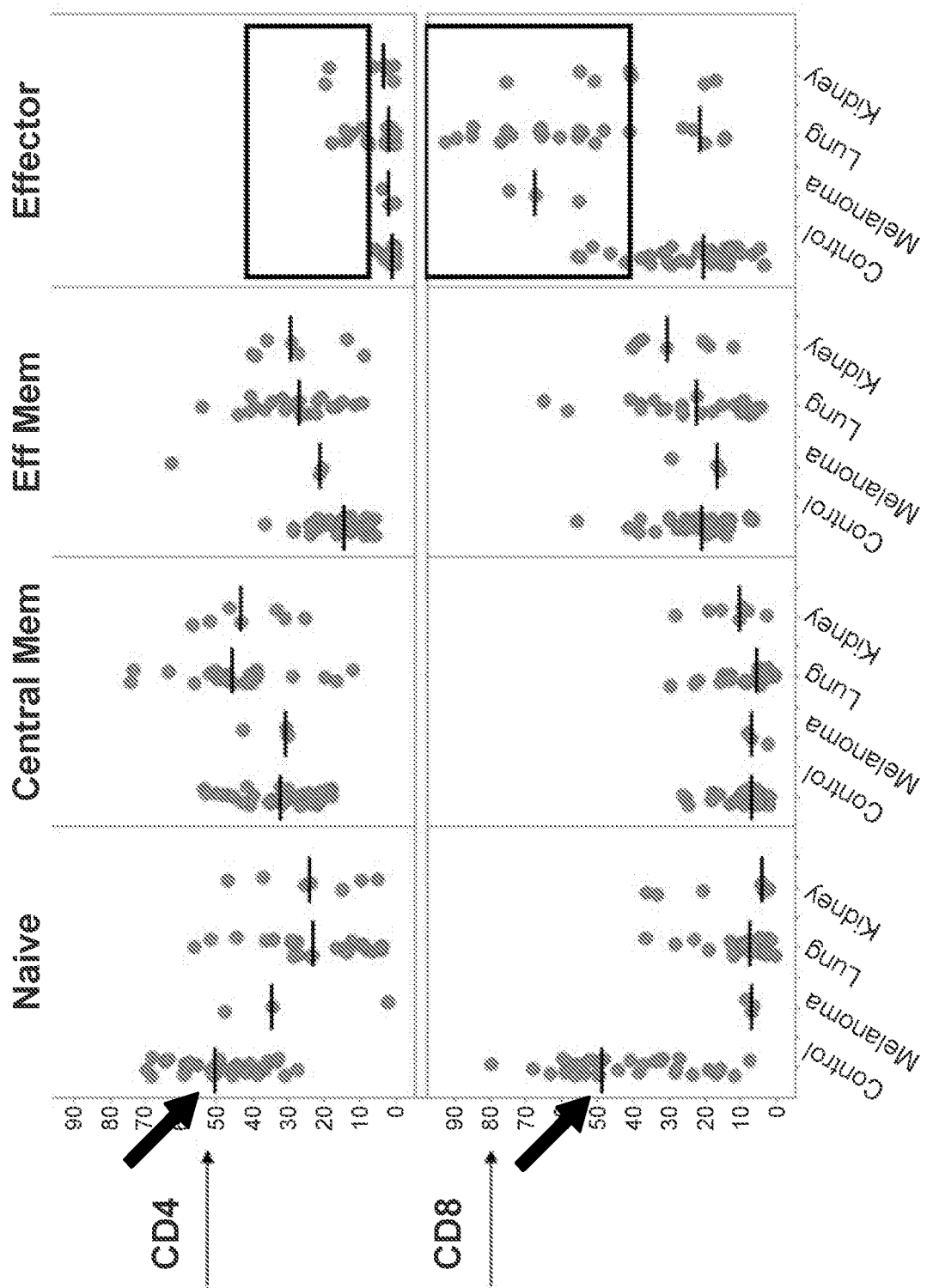
FIG. 5A shows the percentage of naïve, central memory, effector memory and effector T cells in CD4+ T cells (top) and CD8+ T cells (bottom) in healthy subjects ("control"; left population), melanoma cancer patients ("melanoma"), lung cancer patients ("lung") and kidney ("kidney") cancer patient, shown from left to right.
Figure 5B:
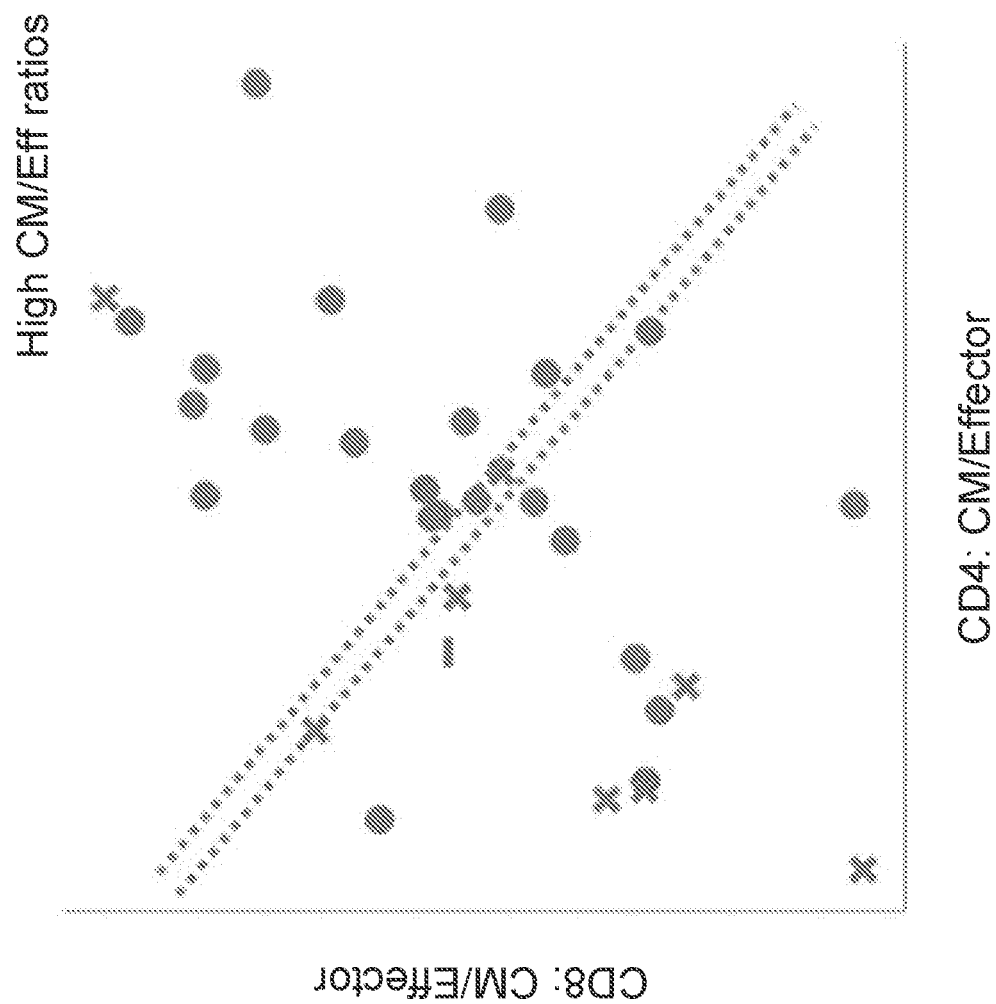
FIG. 5B shows the ratio of CM/Teff T cells in CD8+ T cells as a function of the ratio in CD4+ cells for cancer patients (every spot represents the ratios in a given cancer patient). Crosses represent patients who progressed at 8 weeks of treatment with an anti-PD-1 agent, and "-" indicates a patient for whom no data was available at 8 weeks.

The results are shown in FIG. 5A. Ratios of central memory T cells: effector T cells were plotted as described in Example 4 with an indication of those patients that progressed at 8 weeks. The results are shown in FIG. 5B, and indicate that patients who progressed after 8 weeks of treatment are mostly patients that have lower ratios of CD4+ and CD8+ central memory Tcells:effector T cells.

The results show higher CM/Eff T cell ratios in patients who show a response to anti-PD1 agents. Thus, circulating central memory to effector T cell ratios can be used as a biomarker predicting the response of a cancer patient to a checkpoint inhibitor, e.g., a PD-1 inhibitory agent.

Example 6

Circulating T Cell Subpopulations Correlate with Immune Responses at the Tumor Site and Clinical Response to PD1 Inhibition in Non-Small Cell Lung Cancer

SUMMARY

Agents targeting the PD-1-PD-L1 axis have transformed cancer therapy. Factors that influence clinical response to PD-1-PD-L1 inhibitors include tumor mutational burden, immune infiltration of the tumor and local PD-L1 expression. To identify peripheral correlates of the anti-tumor immune response in the absence of checkpoint blockade, a retrospective study of circulating T cell subpopulations and matched tumor gene expression in melanoma and non-small cell lung carcinoma (NSCLC) patients was conducted. Both melanoma and NSCLC patients whose tumors exhibited increased inflammatory gene transcripts presented high CD4+ and CD8+ central memory T cell (CM) to effector T cell (Eff) ratios in blood. Consequently, CM/Eff T cell ratios in a second cohort of NSCLC were evaluated.

The data showed that high CM/Eff T cell ratios correlated with increased tumor PD-L1 expression. Furthermore, of the 22 patients within this NSCLC cohort who received nivolumab, those with high CM/Eff T cell ratios, had longer progression-free survival (PFS) (median survival: 91 vs. 215 days). These findings show that by providing a window into the state of the immune system, peripheral T cell subpopulations inform about the state of the anti-tumor immune response and identify potential blood biomarkers of clinical response to checkpoint inhibitors in melanoma and NSCLC.

Introduction

Since their initial approval for the treatment of melanoma in 2014, anti-PD1 agents have transformed cancer therapy, more than doubling median overall survival rates for melanoma (Hodi et al. The Lancet Oncology. 2016; 17(11):1558-68) and non-small cell lung cancer (NSCLC) (Hui et al. Annals of Oncology. 2017; 28(4):874-81). It is clear that not every patient or cancer type benefits from an anti-PD1 agent. As the PD1/PDL1 regulatory pathway inhibits the effector activity of T cells, the efficacy of an anti-PD1 agent depends not only on the presence of a counter-ligand to inhibit but more importantly, on the availability of tumor-specific T cells whose activity can be unleashed by the therapeutic agent (Boutros et al. Nat Rev Clin Oncol. 2016; 13(8):473-86).

The quest to identify cancer patients who will benefit from therapy includes several companion and complementary diagnostic assays performed on tumor biopsies. These assays aim to identify PDL1 expression in the tumor and tumor microenvironment (Herbst et al. Nature. 2014; 515 (7528):563-7), and tumor mutation burden (TMB) as a surrogate measure of neoantigen availability (Snyder et al. New England Journal of Medicine. 2014; 371(23):2189-99). In recent findings, the presence of an active immune infiltrate, evaluated through the expression of transcripts associated with CD8+ T cell function, correlates highly with a positive clinical outcome towards anti-PD1 agents (Spranger et al. Nature. 2015; 523(7559):231-5).

The determination of a patient's probability of response to anti-PD1/PDL1 agents is critical to inform a course of treatment and requires the identification of readily assessable biomarkers. While tissue biopsies provide a window into the immune response unfolding within the tumor microenvironment, tumor heterogeneity and the presence of multiple tumor sites can lead to mischaracterization of the magnitude of the anti-tumor immune response (Callea et al. Cancer Immunology Research. 2015; 3(10):1158-64).

In addition, the extent of this response depends on the state of the host's immune system. Factors such as genetic background, age, gender and therapies such as chemotherapy and radiotherapy affect the immune system (Chen et al. Immunity. 2013; 39(1):1-10). This heterogeneity creates a need to improve the evaluation of the status of the immune system in cancer patients and its associated clinical outcomes. The dynamic nature of tumor evolution in response to therapy means that long-lasting clinical responses require an immune system fit to adapt to this changing environment (Gatenby et al. Cold Spring Harbor perspectives in medicine. 2017).

An effective immune response towards a tumor requires neoantigen availability (Snyder et al. New England Journal of Medicine. 2014; 371(23):2189-99) and presentation to T cells, and subsequently the entry of antigen-exposed, activated T cells to the tumor. The tumor, in turn, can downregulate the immune response by expressing PDL1, which activates a regulatory mechanism in the T cell through its interaction with PD1 (Boutros et al. Nat Rev Clin Oncol. 2016; 13(8):473-86).

To determine if blood T cell subpopulations reflect the immune response against the tumor, a cross-sectional, a retrospective analysis of peripheral T cells and matched tumor gene expression in melanoma and NSCLC samples collected before checkpoint inhibitors became part of the standard of care was performed. A correlation between the degree of expression of inflammatory transcripts in the tumor and the percentages of circulating central memory (CM) and Effector (Eff) CD4+ and CD8+ T cells, expressed as independent CD4+ and CD8+CM/Eff T cell ratios. High CM/Eff T cell ratios correlate with inflamed tumors was observed.

Given that tumor inflammation correlates with good clinical response to checkpoint inhibitors, whether high CM/Eff T cell ratios correlate with clinical outcome in a cohort of nivolumab-treated NSCLC patients was tested. In this cohort, those patients with high CM/Eff T cell ratios experienced more prolonged PFS. Given that melanoma and NSCLC patients with inflamed tumors, as well as NSCLC patients with longer PFS have high CM/Eff T cell ratios. Thus, measurement of these ratios in an easily accessible peripheral blood sample is a convenient biomarker of the state of the T cell arm of the immune system. These findings represent progress in the characterization of peripheral immunity, immune state and its relationship to the inflammatory status of the tumor.

Methods

Tissues and PBMC

Banked PBMC and matched flash frozen tumor samples from melanoma and NSCLC patients were obtained in collaboration with M2GEN and Moffitt Cancer Center (Tampa, FL) and consented through their Total Cancer Care protocol. Control PBMC were obtained from the Bristol-Myers Squibb employee volunteer blood donation program (TABLE 3).

TABLE 3

Patient characteristics and demographics

| COHORT | PATIENTS (N) | MEAN AGE (SD), Y | MALE, N | STAGE II, N (%) | STAGE III, N (%) | STAGE IV, N (%) |
| --- | --- | --- | --- | --- | --- | --- |
| CONTROL | 27 | 54.9 (8.5) | 12 | | | |
| MELANOMA | 43 | 63.7 (15.0) | 31 | 1 (2.3) | 17 (39.5) | 25 (58.1) |
| NONSQUAMOUS NSCLC | 40 | 65.7 (11.8) | 15 | 16 (4.00) | 12 (30.0) | 12 (30.0) |

For the second NSCLC cohort, blood samples we obtained from 57 patients with NSCLC from a commercial vendor (MT group, CA). A subset of these samples (n=22) was from patients before receiving nivolumab as part of their clinical care. A second blood sample and clinical evaluation was obtained between 8 and 12 weeks after the start of the treatment. Control blood samples were obtained from the BMS employee volunteer blood program and processed simultaneously.

Flow Cytometry

PBMC were stained for viability with Near Infrared dye (Molecular Probes), blocked and incubated in an antibody mix containing anti-CD127-AF488 (Clone A0195D5), anti-PD1-PE (Clone EH12), anti-CD8-APC-R700 (RPA-T8), anti-CD28-BV650 (CD28.2), anti-CCR7-BV421 (G043H7), anti-CD25-PECy7 (M-A251), anti-PD-1-PE (EH12), anti-CD45RA-BUV395 (HI100) anti-CD4-BUV495 (SK3) and anti-CD3 BUV737 (SK7).

Whole blood samples were collected and shipped overnight. Whole blood was then stained for viability with Near Infrared dye (Molecular Probes) followed by wash and surface staining with an antibody mix containing: anti-CD45-BV480 (Clone HI30), anti-CD4-AF700 (SK3), anti-CD8-BUV395 (RPA-T8), anti-CD3-BUV496 (UCHT1), anti-CCR7-BV711 (G043H7), anti-PD-1-APC (MIH4) and anti-CD45RO-BV421 (UCHL1). All samples were read on a BD Fortessa instrument and analyzed with FlowJo. Spanning Tree Progression of Density Normalized Events (SPADE) analysis (Qiu et al. Nat Biotech. 2011; 29(10): 886-91) were implemented on Cytobank (www.cytobank.org). Independent clustering of either CD4+ or CD8+ T cells used CD45RA, CCR7 and CD28. Both the circles and color scale denote the number of cells in the cluster.

Gene Expression and Inflammatory Signature

Total RNA was isolated from frozen tumor using AllPrep DNA/RNA/miRNA kit (Qiagen, Valencia, CA) following manufacturer's recommended protocols. After assessing RNA quality, sequencing libraries were made using the TruSeq Stranded mRNA HT kit (illumina, San Diego, CA). Libraries were run on an illumina HiSeq 2500 at EA Genomics Services. Paired end FASTQ files were stored in AWS S3, and all analysis took place on AWS EC2 c3.8x large instances created by StarCluster (Riley J. Star Cluster. http://star.mit.edu/cluster/. 2018).

Gene and isoform expression was calculated using RSEM (Li & Dewey BMC Bioinformatics. 2011; 12(1):323) v1.1.13 and the UCSC hg19 genome annotation. An additional step of calculating gene and isoform quantile normalized read counts was performed using a custom Perl script Inflammation gene expression scores were calculated based on the gene signature described in Spranger et al. (Nature. 2015; 523(7559):231-5) by calculating the mean of the log 2, centered normalized data. Genes included in the signature include CD8A, CCL2, CCL3, CCL4, CXCL9, CXCL10, ICOS, GZMK, IRFV1, HLA-DMA, HLA-DOA HLA-DOB. The scores where then split based on quantiles of the normal distribution as inflamed, intermediate and non-inflamed.

Statistics and Visualizations

Figure 6A:
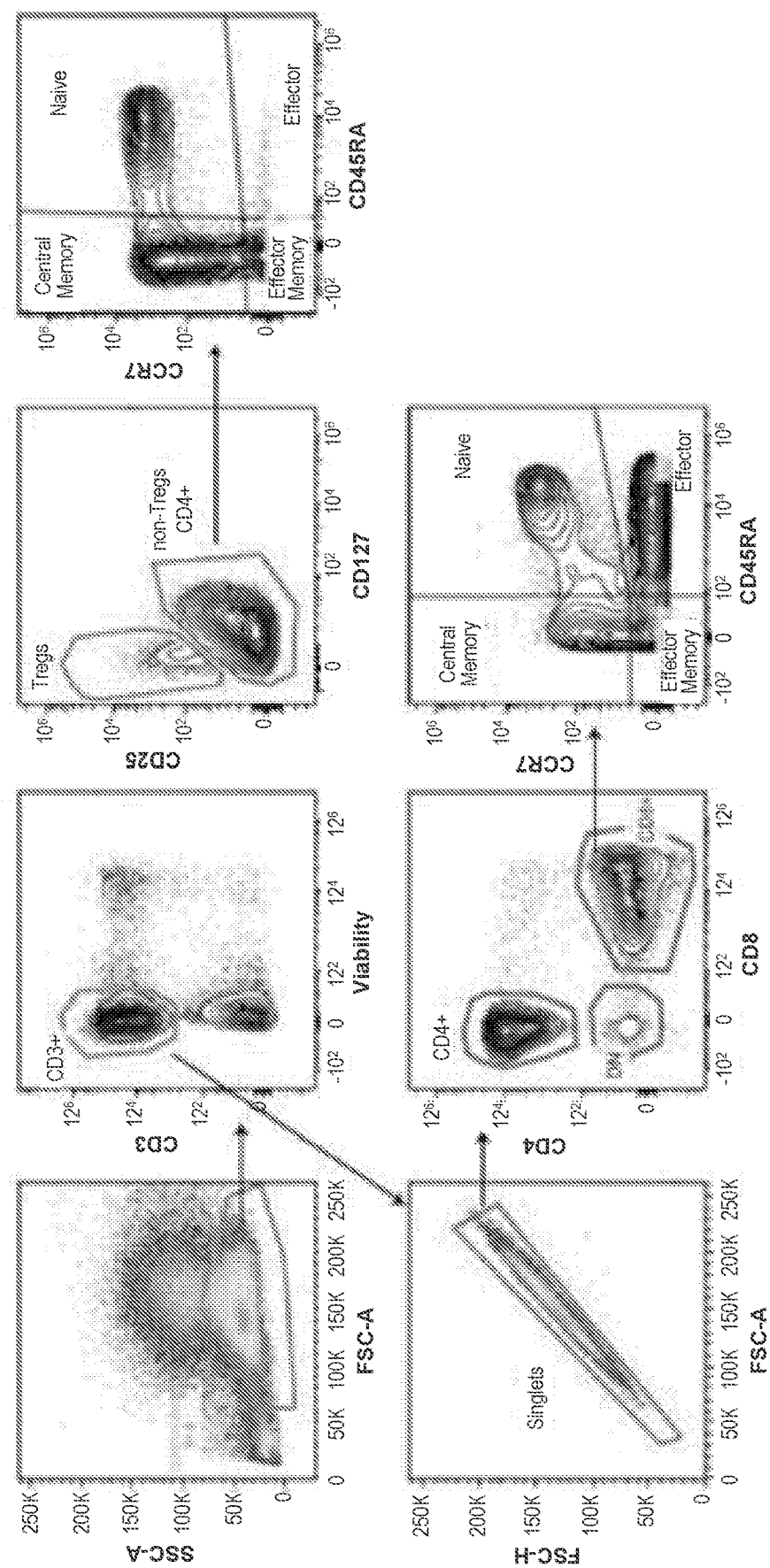
FIGS. 6A and 6B shows that peripheral T cell subpopulations evidence an ongoing immune response in cancer patients.
Figure 8A:
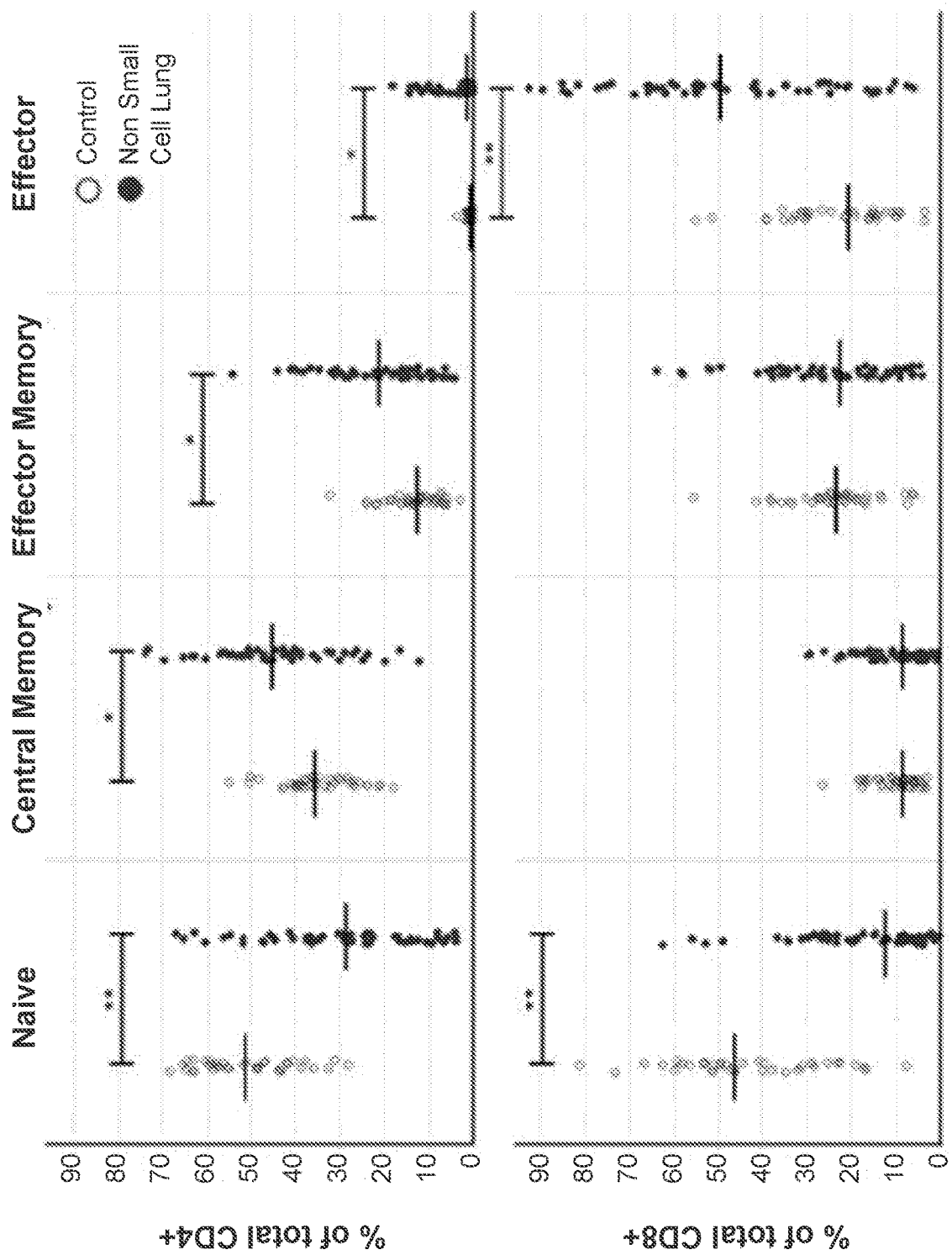
Figure 9:
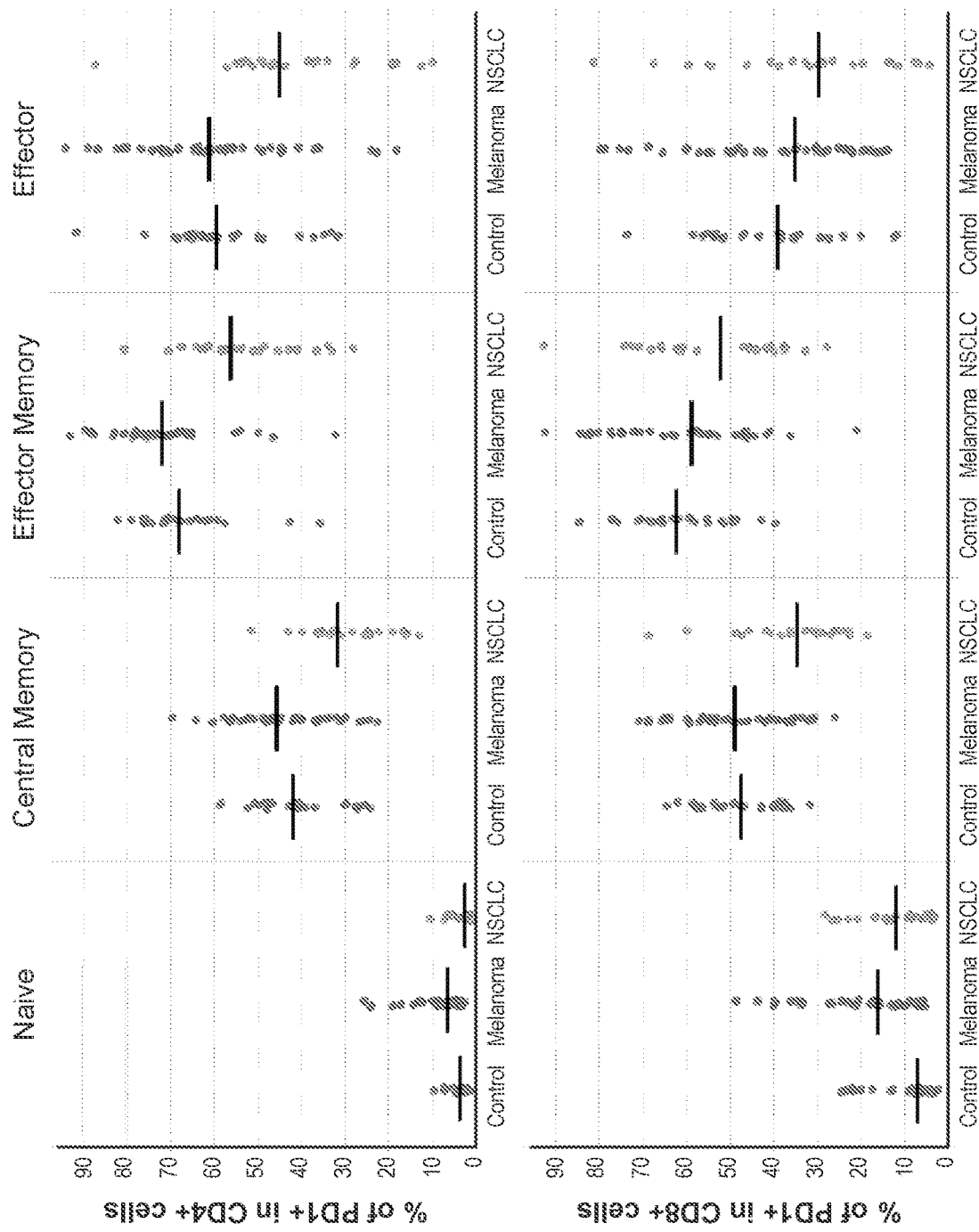
FIG. 9 shows percentage of PD1+ cells per T cell subpopulation in the M2GEN cohort. The horizontal line marks the median for each subpopulation. Percentages for control, melanoma and NSCLC populations are shown from left to right, respectively, for each type of cell.
Figure 12:
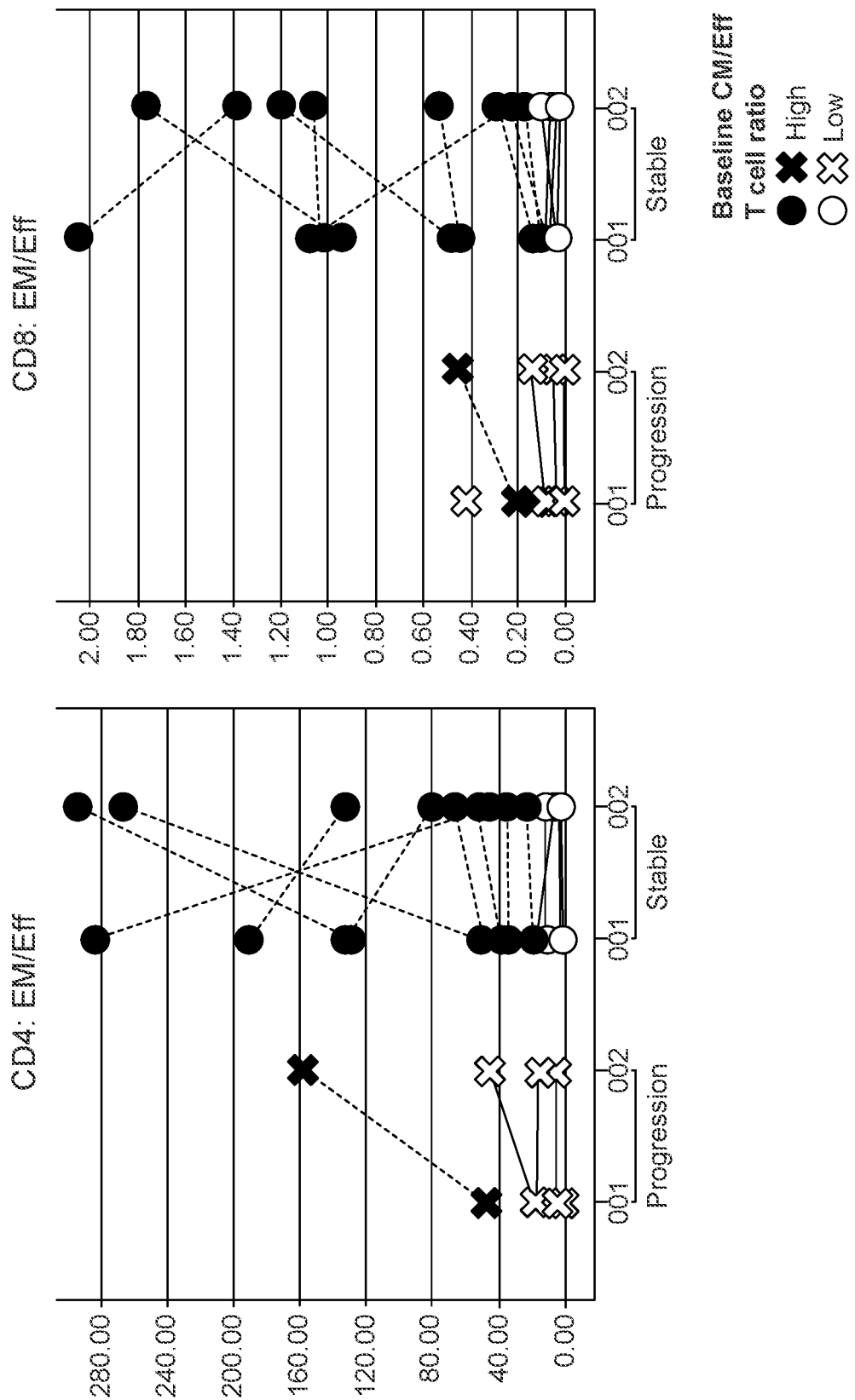
FIG. 12 shows the change in CM/Eff T cell ratios three months after nivolumab-treatment initiation. Patients are separated by physician-reported response to treatment evaluated at the time of the second blood draw.

Comparisons of T cell subpopulations were performed using Student's t test. For non-normal distributions, data was log-transformed before t test. All reported p-values were corrected for multiple comparisons (FIG. 6A and FIG. 8A).

Fischer's exact test was used for the analysis of 2×2 contingency tables for CM/Eff T cell ratios by inflammation state and PDL1 TPS (separately).

For PFS analysis of patients undergoing treatment with nivolumab, all patients had at least 90 days of follow up after first dose. PFS was calculated from the first day of nivolumab infusion until physician-confirmed disease progression (clinical or CT confirmed) by a scientist blind to the patient's biomarkers characteristics. Right-censored data was used to obtain Kaplan-Meier survival estimates and Wilcoxon p-values. All statistical analysis were performed in JMP 13.

Results

Circulating T cells in melanoma and nonsquamous NSCLC patients show evidence of ongoing immune responses: Patients with cancer have circulating T cells specific for tumor antigens (Gros et al. Nat Med. 2016; 22(4):433-8). Consequently, we postulated that the circulating T cell pool would reflect the immune responses to melanoma and NSCLC. To evaluate this principle in the absence of checkpoint inhibitors, a cross-sectional, retrospective study was performed using T cell subpopulations in archived PBMC from 43 melanoma and 40 NSCLC patients (all of them nonsquamous NSCLC). All of the patients had available matched tumor tissue, and none of them had prior treatment with checkpoint agents (TABLE 3 and FIG. 6A).

Figure 6B:
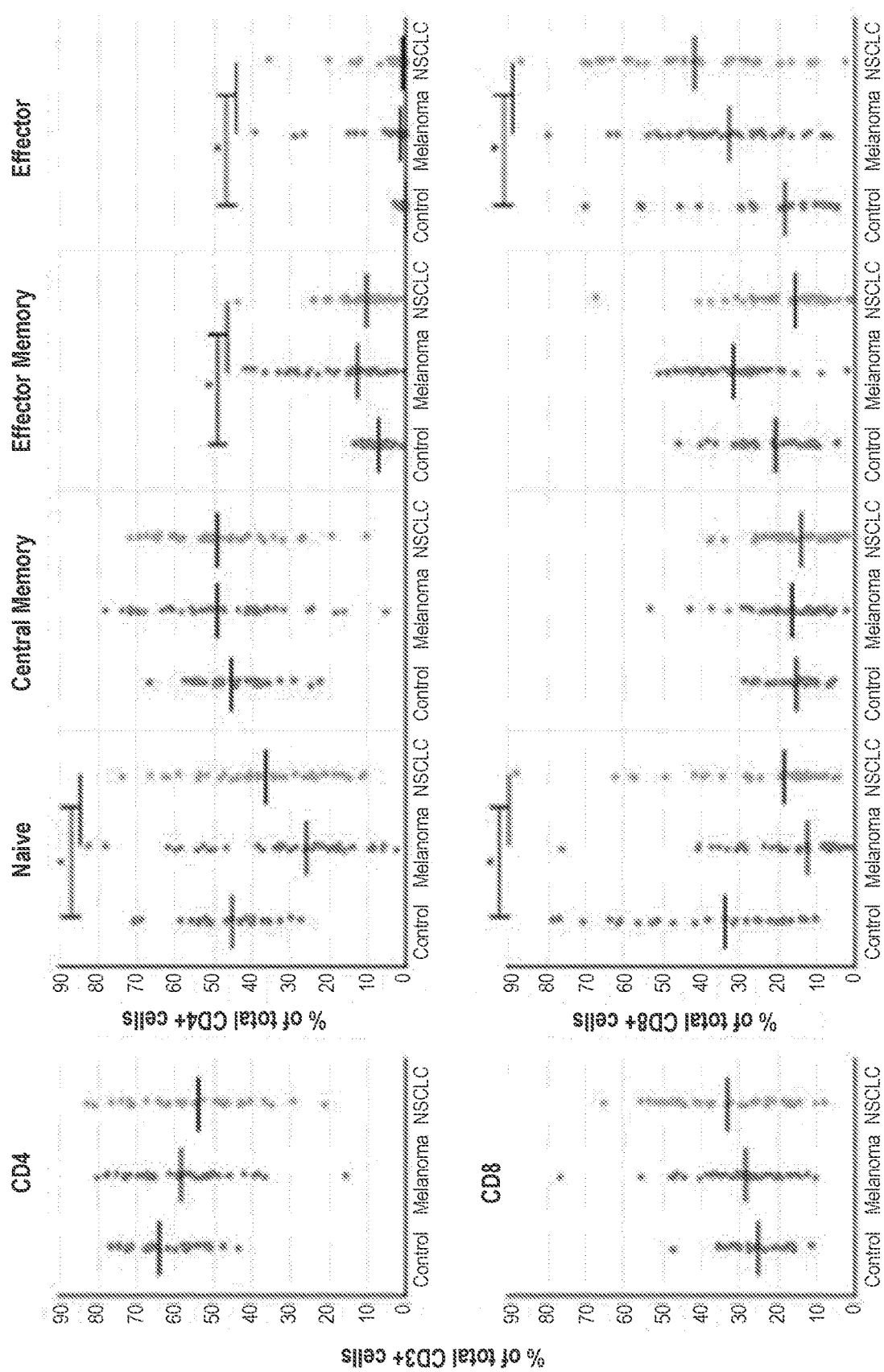

Analysis of T cell subpopulations revealed that as a group, PBMC from cancer patients presented a decrease in the percentages of both CD4+ and CD8+ naïve T cells, accompanied by an increase in the percentages of EM and Eff CD4+ and Eff CD8+ T cells compared to control samples (FIG. 6B). These findings were consistent with the presence of an ongoing immune response in these patients as observed in patients with autoimmunity (Manjarrez-Orduño et al. ImmunoHorizons. 2017; 1(7):124-32).

Figure 7A:
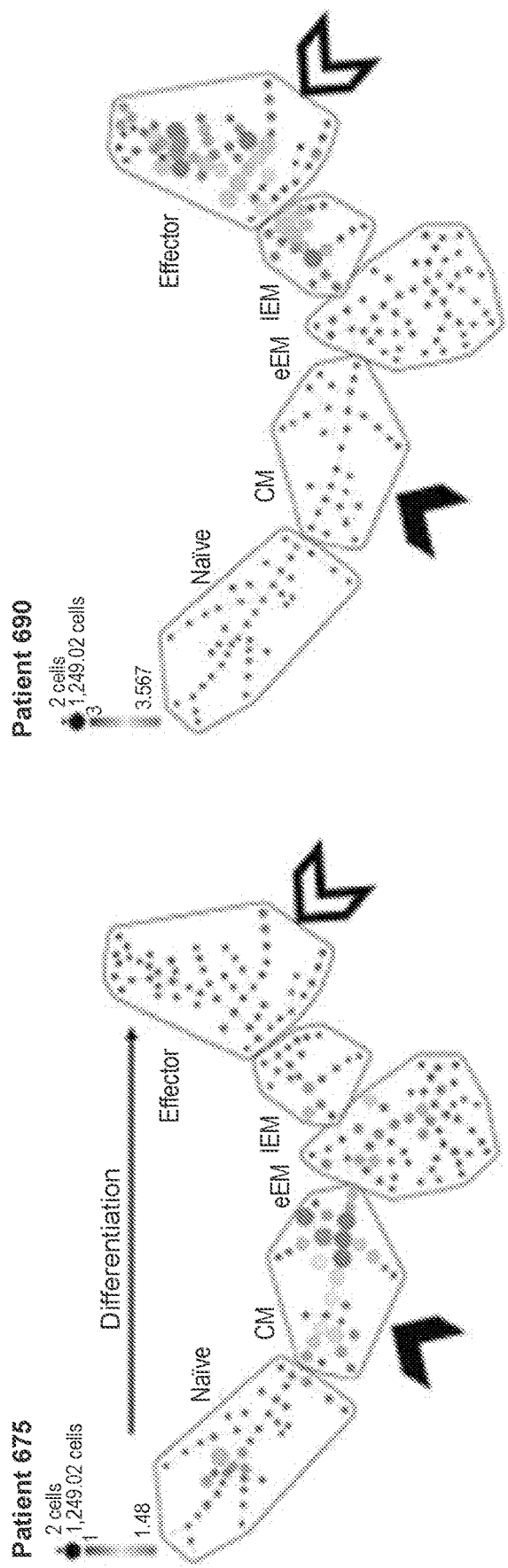
FIGS. 7A, 7B and 7C shows that local immune responses in melanoma and NSCLC correlate with circulating CM/Eff T cell ratios.

Association of circulating T cell profiles with the local immune response in melanoma and nonsquamous NSCLC: To assess the T cell differentiation patterns present in these patients, SPADE on the flow cytometry data was implemented (see Methods). Clustering of either CD4+ or CD8+ T cells using the differentiation markers CD45RA, CCR7 and CD28 showed that in cancer patients, the circulating antigen-experienced T cells present either CM-early Effector Memory or Eff phenotypes (FIG. 7A), also reflected by the inverse relationships between CM and Eff subpopulations.

Next, how the circulating T cell subpopulations reflect the local immune state observed in the tumors was evaluated. Matched frozen tumor tissues were used to evaluate gene expression profiles of immune-associated genes. Tumors were defined as inflamed, intermediate and non-inflamed based on quantiles of inflammation gene signature scores. Through further analysis of the inflamed versus non-inflamed tumors a correlation was observed between tumor inflammation and the percentages of circulating central memory and effector T cells, which while similar in magnitude, showed a different direction.

Figure 7C:
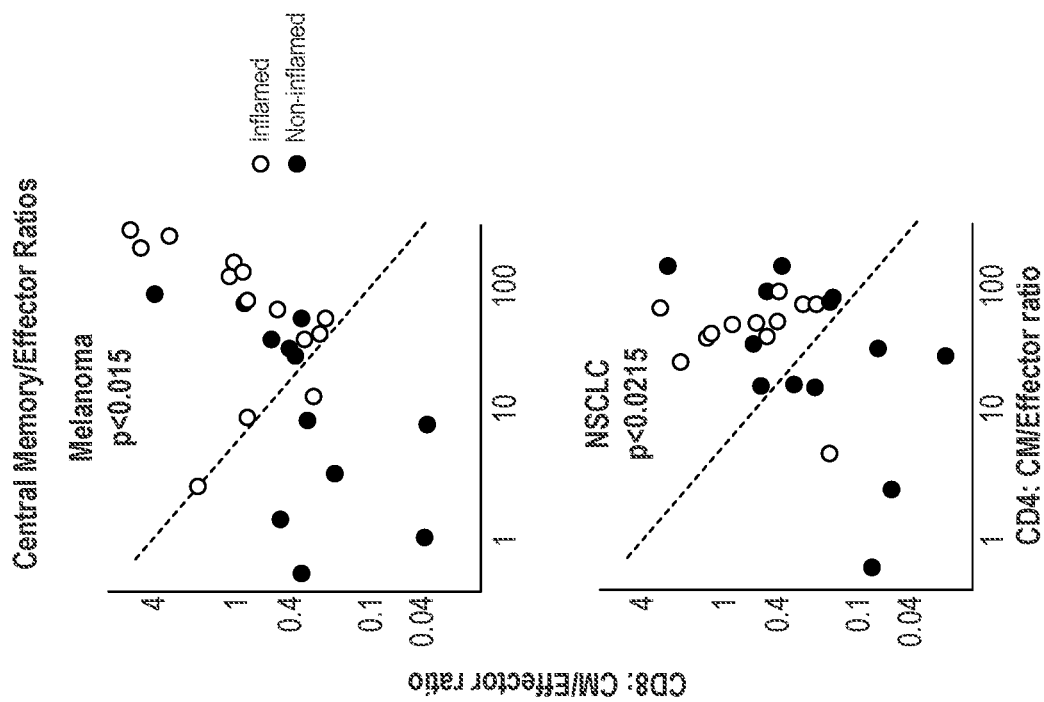
Figure 7B:
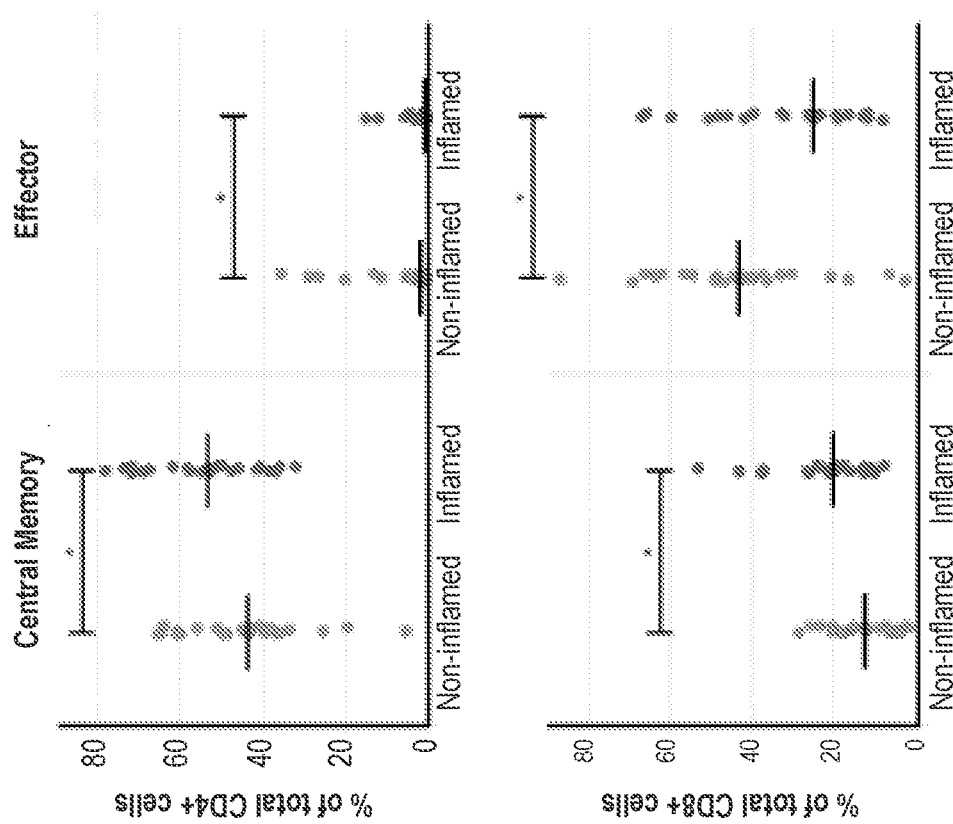

The peripheral blood populations that showed a positive correlation with inflamed tumors were not the effector T cell subpopulations populations, but CM, for both CD4+ and CD8+ T cells (FIG. 7B).

Given the inverse relationship between CM and Eff T cells, CM/Eff ratios were calculated for both CD4+ and CD8+ T cells (FIG. 7C). Patients with inflamed tumors by gene expression had a tendency towards high CM/Eff ratios (upper right corner).

CM/Eff ratios in patients with high inflammation scores are similar to those of the healthy control samples used in this study. Consequently, the $90^{th}$ percentile of control samples was used to distinguish between low and high CM/Eff ratios, observing that the inflamed melanoma and NSCLC tumors have high CM/Eff ratios compared to those with non-inflamed tumors.

Circulating CM/Eff T cell ratios in NSCLC are associated with longer progression-free survival in response to checkpoint inhibitors: To evaluate CM/Eff T cell ratios as a tool to evaluate the status of the T cell arm of the immune system, blood was collected from a second cohort of NSCLC patients (n=57). The analysis of these confirmed that the reduction of the naïve compartment and the expansion of Eff T cell subpopulations, both in CD4+ and CD8+ T cells, was a reproducible finding (FIG. 8A).

PDL1 is an interferon gamma-induced gene (Garcia-Diaz et al. Cell reports. 2017; 19(6):1189-201). Accordingly, whether the interferon gamma produced during anti-tumor immune responses lead to the upregulation of PDL1 was evaluated.

In the 23 patients where PDL1 expression was measured, a bimodal distribution in the percentage of PDL1 tumor proportion score (% TPS) (FIG. 8B) was observed. Based on this pattern, patients were divided at the antimode (25% TPS) as PDL1$^{neg/low}$ and PDL1$^{high}$. High CM/Eff T cell ratios, which had previously been found associated with higher inflammatory signature (FIG. 7C), correlated with high PDL1 expression in the tumor (FIG. 8C, Fisher's exact p<0.025).

A subset of these NSCLC patients went on to receive nivolumab as part of their clinical care (n=22). Those patients with high CM/Eff T cell ratios at baseline had an extended PFS compared to those patients with low CM/Eff T cell ratios (FIG. 8D, Wilcoxon test p<0.05, median survival time "low" ratio: 91 days, "high" ratio 215 days).

A second blood sample, obtained around three months after the initiation of nivolumab treatment did not show major changes in CM/Eff T cell ratios in patients categorized as "low", in contrast to those patients classified as "high" (FIG. 10). Only seven of the original 11 "low" patients were still in nivolumab treatment, in contrast to ten of the 11 "high" patients.

DISCUSSION

The data presented indicates an correlation between circulating CM/Eff T cell ratios and tumor inflammation in melanoma and NSCLC, as well as with increased PDL1 expression at the tumor and longer PFS in response to nivolumab treatment in NSCLC. To the best of our knowledge, this is the first time that circulating T cell subpopulations are identified as predictive biomarkers of response to checkpoint inhibitors in NSCLC.

The association between higher frequency of CM T cells (CD4 and CD8) and an increased tumor inflammatory profile is consistent with reports that CM T cells are the primary repository of the immunogenic experiences of a lifetime (Berger et al. The Journal of clinical investigation. 2008; 118(1):294-305, Wherry et al. Nature immunology. 2003; 4(3):225-34). The inverse relationship between the frequency of Eff T cells in circulation and the inflammation signature in the tumor was nevertheless surprising and unexpected and may reflect the presence of terminally differentiated T cells that are unable to reach the tumor.

Rather than reflecting the immune response against the tumor, we hypothesize that CM/Eff ratios are a way to evaluate the status of the immune system. In this model, immune state evaluated by CM/Eff ratios would be associated with the capacity of a subject to mount an immune response against the tumor that checkpoint inhibitors can potentiate. This model is congruent with the high sensitivity of this analysis to detect cancer patients who have inflamed tumors (>90%, FIG. 7C). Nevertheless, its low specificity highlights the multifactorial nature of the anti-tumor response, as other factors, such as TMB, also play a role in the anti-tumor response (Goodman et al. Molecular cancer therapeutics. 2017; 16(11):2598-608).

These findings provide a window into how the status of the immune system affects the anti-tumor response. Extended clinical responses to checkpoint inhibitors depend on the presence of tumor-specific T cells, and the ability of the immune system to co-evolve with the tumor. Thus, shifting the predominant T cell response as the dominant antigen disappears or mutates (Purroy et al. Cold Spring Harbor perspectives in medicine. 2017; 7(4)). Under this model, increased immunological pressure towards the tumor (increased inflammation signature) may drive the upregulation of PDL1 as an immunosuppressive tumor-survival mechanism (Taube et al. Science translational medicine. 2012; 4(127):127ra37), as observed in the patients with high CM/Eff T cell ratios.

These results align with previous reports that the percentages of CD4 and CD8+ T cell memory correlate with clinical response in melanoma patients treated with ipilimumab (Tietze et al. European journal of cancer (Oxford, England: 1990). 2017; 75:268-79, Subrahmanyam et al. Journal for immunotherapy of cancer. 2018; 6(1):18). Moreover, a recent analysis of four melanoma patients (two with stable disease, one progressive disease, and one partial response) show an increase of central memory CD4+ T cells in the two patients with longer survival times (Takeuchi et al. International Immunology. 2017:dxx073-dxx). This data is in line with a recent report of peripheral immune cells and its correlation with response to checkpoint inhibitors in melanoma which also found an association between increased CD8+CM T cells and clinical response (Krieg et al. Nature medicine. 2018). However, the highly overlapping ranges of the populations limit their use to identify patients with higher probabilities of responding to checkpoint inhibitors. Our data shows how CD4+ and CD8+CM and effector T cells are a bellwether of responses to checkpoint inhibitors, presumably because all of them contribute to the anti-tumor responses (Ahrends et al. Immunity. 2017; 47(5):848-61.e5, Klebanoff et al. Proc. Nat'l Acad Sci USA. 2005; 102(27): 9571-6). The integration of all these correlates of T cell status into a simple parameter, allows us to identify better those NSCLC patients most likely to experience clinical benefit from checkpoint inhibitor therapy.

There is a clear need to grasp the mechanisms underlying primary resistance and short-lived clinical responses to checkpoint inhibitors. Our data suggest that the state of the T cell arm of the immune system, measured by the relative frequency of CM/Eff T cell ratios can be a contributing mechanism. Even more, improving the number of patients who can benefit from immune therapy requires a comprehensive analysis of the relative contributions of T cell subpopulations to anti-tumor responses. This challenge includes understanding whether a reduced naïve T cell repertoire contributes to functional T cell depletion, and the capacity of CM T cells to replenish the T cell repertoire (Klebanoff et al. Proc. Nat'l Acad Sci USA. 2005; 102(27): 9571-6). At a functional level, high levels of the pro-apoptotic molecule Bim in $PD1^+CD11a^+$ $CD8^+$ T cells of melanoma patients associate with shorter survival after anti-PD1 treatment, presumably because Bim may induce apoptosis of anti-tumor specific T cells (Dronca et al. JCI Insight. 2016; 1(6)). Early pharmacodynamics effects of anti-PD1 associated with clinical benefit are the extent of expression of the proliferation marker ki67 in $PD1^+$ T cells (Huang et al. Nature. 2017; 545:60, Kamphorst et al. Proc. Nat'l Acad Sci USA. 2017; 114(19):4993-8) or of particular memory subtypes (Yan et al. JCI Insight. 2018; 3(8)). An integrated analysis of these T cell subpopulations and their relationship to each other would provide a better understanding of the mechanisms behind primary resistance to anti-PD1 therapy. Along with this line, a comprehensive analysis of the TCR repertoire together with gene expression in patients during checkpoint therapy would shed light on this particular question. Despite all of the question it casts, this method to evaluate the immune system provides an easily accessible circulating biomarker to add to a comprehensive evaluation that already includes TMB and PDL1. Altogether, these assays may enable a better prediction of which patients will respond to checkpoint inhibitors, as well as those who may obtain more benefit from other agents.

What is claimed is:

1. A method of treating a subject having cancer, comprising administering an antibody that specifically binds PD-1 (anti-PD-1 antibody) or PD-L1 (anti-PD-L1 antibody) to a subject identified as having (a) a circulating central memory T Cells (TCM): circulating T effector memory cells (Teff) ratio that is similar to or higher than the TCM: Teff ratio in the top 90% of healthy subjects; or
both (i) a circulating CD4+ TCM: circulating CD4+ Teff ratio and (ii) a circulating CD8+ TCM: circulating CD8+ Teff ratio that are similar to or higher than those, respectively, in the top 90% of healthy subjects;
wherein the anti-PD-1 antibody or anti-PD-L1 antibody is only administered to the subject if more than or equal to 1% of tumor cells in the subject express PD-L1 and wherein the Teff cells are negative for CD45RA and CCR7.

2. The method of claim 1, wherein the anti-PD-1 antibody is selected from the group consisting of nivolumab, pembrolizumab, PDR001, REGN2810, AMP-514 (MEDI0608), and BGB-A317.

3. The method of claim 1, wherein the anti-PD-L1 antibody is selected from the group consisting of atezolizumab, durvalumab, and avelumab.

4. The method of claim 1, wherein the cancer or tumor is a melanoma, a non-small cell lung cancer (NSCLC), or kidney cancer.

5. The method of claim 1, wherein
(i) the TCM are CD4+ TCM cells and the Teff are CD4+ Teff cells; or
(ii) the TCM are CD8+ TCM cells and the Teff are CD8+ Teff cells; or,
(iii) the TCM are CD4+ TCM cells and CD8+ TCM cells, and the Teff are CD4+ Teff cells and CD8+ Teff cells.

6. The method of claim 1, wherein the TCM are TCM cells that are CCR7+ and CD45RA-.

* * * * *